United States Patent
Moy et al.

(10) Patent No.: US 11,957,775 B2
(45) Date of Patent: Apr. 16, 2024

(54) PERSONAL CARE FORMULATIONS

(71) Applicant: Colgate-Palmolive Company, New York, NY (US)

(72) Inventors: Melissa Moy, Staten Island, NY (US); Ewelina Lesniak, Linden, NJ (US); Kristina Fabijanic, Jersey City, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/743,895

(22) Filed: May 13, 2022

(65) Prior Publication Data

US 2022/0362121 A1 Nov. 17, 2022

Related U.S. Application Data

(60) Provisional application No. 63/201,791, filed on May 13, 2021.

(51) Int. Cl.
*A61K 8/36* (2006.01)
*A61K 8/34* (2006.01)
(Continued)

(52) U.S. Cl.
CPC ............... *A61K 8/365* (2013.01); *A61K 8/34* (2013.01); *A61K 8/345* (2013.01); *A61K 8/36* (2013.01); *A61K 8/44* (2013.01); *A61K 8/60* (2013.01); *A61K 8/9789* (2017.08); *A61Q 19/008* (2013.01); *A61Q 19/08* (2013.01)

(58) Field of Classification Search
None
See application file for complete search history.

(56) References Cited

U.S. PATENT DOCUMENTS 7,547,454 B2  6/2009  Gupta
8,017,138 B2  9/2011  Gross
(Continued)

FOREIGN PATENT DOCUMENTS

CA    3059291 A1 * 10/2018 ............. A61K 31/56
KR    101985381    6/2019
(Continued)

OTHER PUBLICATIONS

Soleymani et al., A practical approach to chemical peels J Clinical and Aesthetic Dermatology 2018.
(Continued)

*Primary Examiner* — Kyung S Chang
(74) *Attorney, Agent, or Firm* — Krisanne Lane

(57) ABSTRACT

Personal care compositions for improving the appearance and/or health of skin are provided herein. In accordance with an aspect, provided is a personal care formulation comprising an alpha hydroxy acid; a beta hydroxy acid; and polyhydroxy acid comprising gluconodeltalactone. According to another aspect, a personal care formulation is provided that comprises an alpha hydroxy acid; a beta hydroxy acid; and polyhydroxy acid, wherein the personal care formulation has a weight ratio of alpha hydroxy acid to polyhydroxy acid is about 5:1 to about 1:4, and wherein the personal care formulation has a weight ratio of beta hydroxy acid to polyhydroxy acid is about 1:1 to about 1:11.

14 Claims, 19 Drawing Sheets

(51) Int. Cl.
      *A61K 8/365*     (2006.01)
      *A61K 8/44*      (2006.01)
      *A61K 8/60*      (2006.01)
      *A61K 8/9789*    (2017.01)
      *A61Q 19/00*     (2006.01)
      *A61Q 19/08*     (2006.01)

(56) References Cited

U.S. PATENT DOCUMENTS

| | | | |
|---|---|---|---|
| 8,178,113 B2 | 5/2012 | Abdullah | |
| 9,101,662 B2 | 8/2015 | Tamarkin et al. | |
| 2008/0241291 A1* | 10/2008 | Abdullah | A61K 8/676 514/474 |

FOREIGN PATENT DOCUMENTS

| | | |
|---|---|---|
| KR | 102212787 | 2/2021 |
| WO | 2015/170063 | 11/2015 |
| WO | 2017/055943 | 4/2017 |
| WO | 2019/058249 | 3/2019 |

OTHER PUBLICATIONS

Cosmelab Co., 2018, "Vita Peeling Pad", Mintel Database GNPD AN: 6155713.
Garden of Wisdom, 2019, "Triple Toning Treatment", Mintel Database GNPD AN: 6781117.
International Search Report and the Written Opinion of the International Searching Authority issued in International Application PCT/US2022/029195 dated Nov. 18, 2022.

* cited by examiner

PERSONAL CARE FORMULATIONS

CROSS-REFERENCE TO RELATED APPLICATION

This application claims the benefit of priority from U.S. Provisional Application No. 63/201,791 filed May 13, 2021, the contents of which are hereby incorporated herein by reference in their entirety.

BACKGROUND

Skincare has many benefits besides recuperating a youthful and glowing appearance. Skin exfoliates dead skin cells naturally every day, however as a result of the aging process, sun damage or exposure to environmental pollutants, the natural peeling process slows and may stop altogether. Our skin becomes dull, dry, flaky and wrinkled. By gently exfoliating the buildup of dead skin, the firmness, the beauty and the even-toned skin are restored.

Many personal care products currently available to consumers are directed primarily to improving the health and/or appearance of skin. For example, there are a variety of topical skin care products available that are directed to delaying, minimizing, or even eliminating skin dryness, skin wrinkling, and other histological changes commonly associated with the aging of skin or environmental damage to human skin. As a result, the sale of personal care products has become a booming business in youth-conscious societies.

There is a growing need for personal care formulations with anti-ageing exfoliating and brightening effects, which bring out a healthy looking radiance while evening skin tone.

BRIEF SUMMARY

Aspects of the invention are directed to personal care formulations and, particularly, to personal care formulations for controlled wounding, by exfoliating the stratum corneum/epidermis of the skin. When the stratum corneum is roughened by internal and external factors, the activation and regeneration of cells underneath the stratum corneum are increased. When keratin peeling is promoted, the skin becomes transparent and soft. The present personal care formulations will not leave any visible scars after their application. In some embodiments, the personal care formulations, of the invention are referred to as exfoliating formulations and/or chemical peels. They are meant to be applied to the human subject in a professional environment. After treatment, the human subject is expected to have a younger looking, smoother, more even-toned skin with a glowing appearance. The personal care formulations of the invention exfoliate the skin, making it smooth and soft, and also improve problems of skin peeling caused by dryness and aging, fortifying the skin barrier.

The personal care formulations of the invention are intended for dermatological topical application and they deliver very low stinging or pain sensation, upon application. The criteria of these personal care formulations are achieved through a combination of alpha hydroxy acids (AHAs), beta hydroxy acids (BHAs), and polyhydroxy acids (PHAs). In addition, the personal care formulations include materials that mitigate stinging, pain are anti-inflammatory and soothing.

The personal care formulations of the invention were evaluated by determining their effect on the surface of the skin. The smoothness of the skin surface was evaluated after treatment with personal care formulations of the invention. The smoothness of the skin was determined with microscopic and nanoscopic techniques, specifically light microscopy (LM) and atomic force microscopy (AFM).

In accordance with an aspect of the invention, provided is a personal care formulation comprising an alpha hydroxy acid; a beta hydroxy acid; and polyhydroxy acid comprising gluconodeltalactone.

According to another aspect of the invention, a personal care formulation is provided that comprises an alpha hydroxy acid; a beta hydroxy acid; and polyhydroxy acid, wherein the personal care formulation has a weight ratio of alpha hydroxy acid to polyhydroxy acid is about 5:1 to about 1:4, and wherein the personal care formulation has a weight ratio of beta hydroxy acid to polyhydroxy acid is about 1:1 to about 1:11.

BRIEF DESCRIPTION OF THE DRAWINGS

The detailed description of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
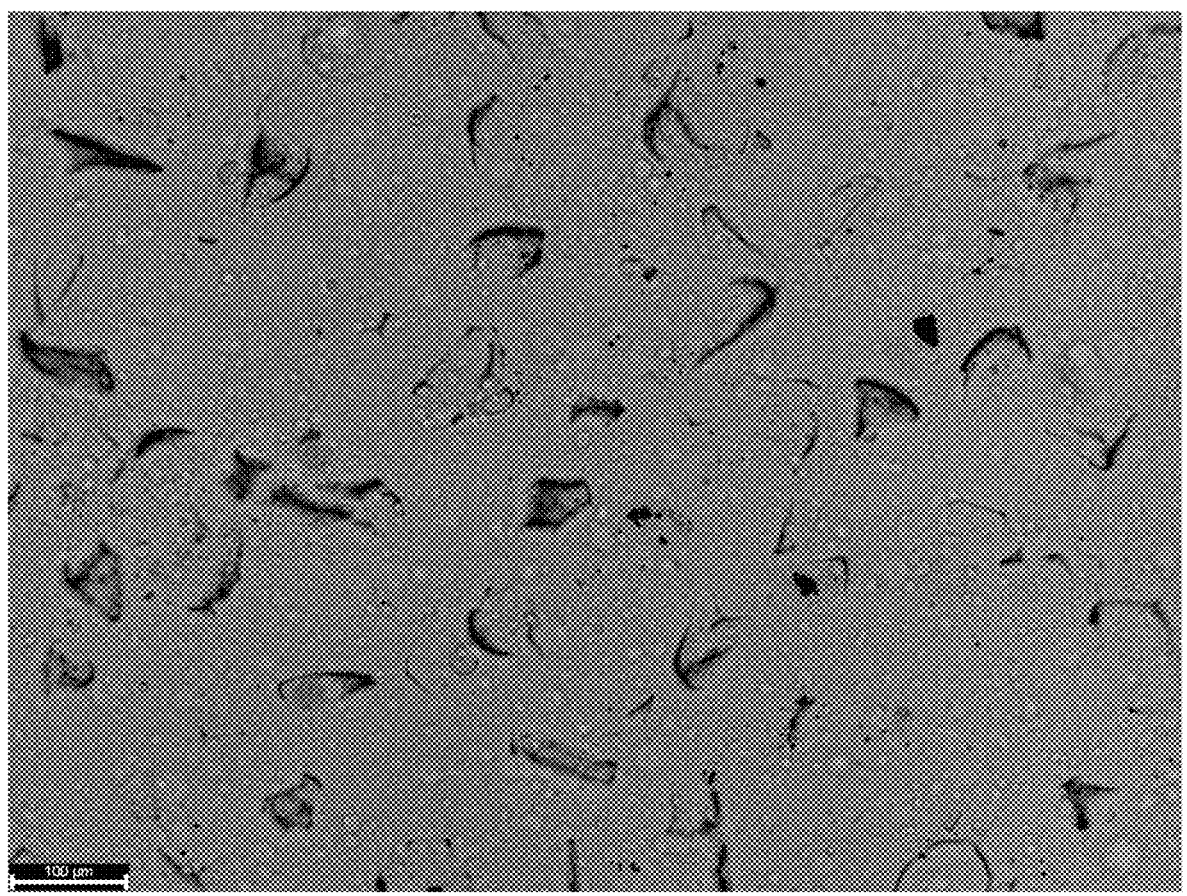
FIG. 1 shows a BrightField image of a skin sample surface before treatment for use as a baseline according to aspects of the invention.
Figure 2:
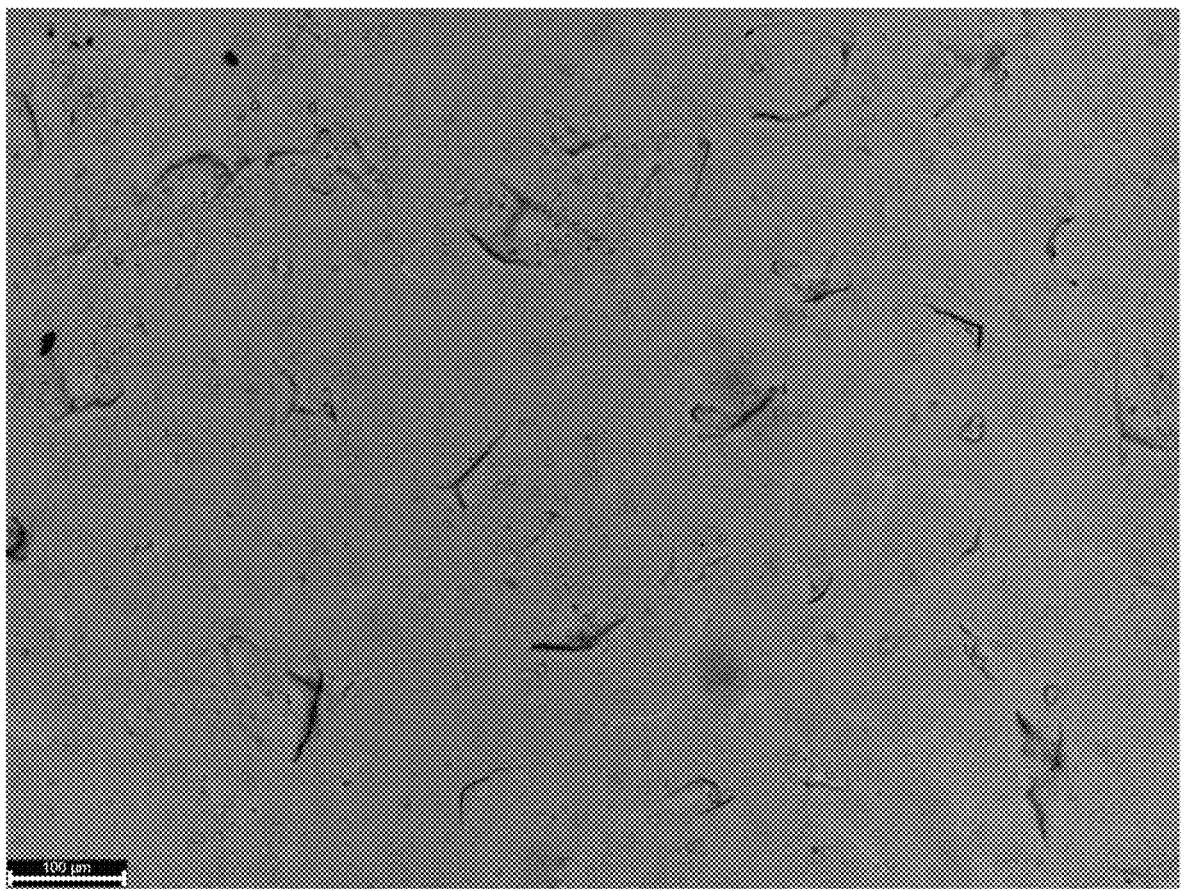
FIG. 2 shows a BrightField image of a skin sample surface after treatment with a first personal care formulation in accordance with aspects of the invention.
Figure 3:
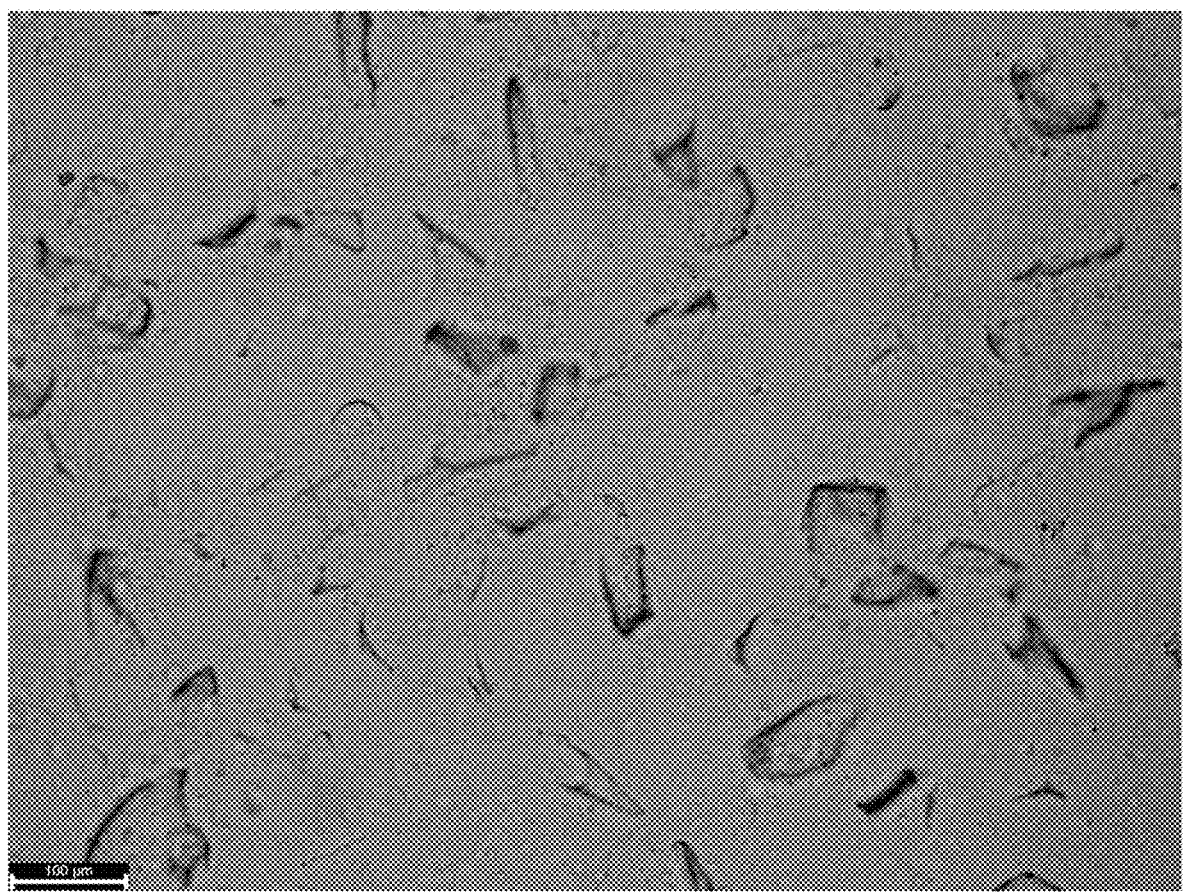
FIG. 3 shows a BrightField image of a skin sample surface after treatment with a second personal care formulation according to aspects of the invention.
Figure 4:
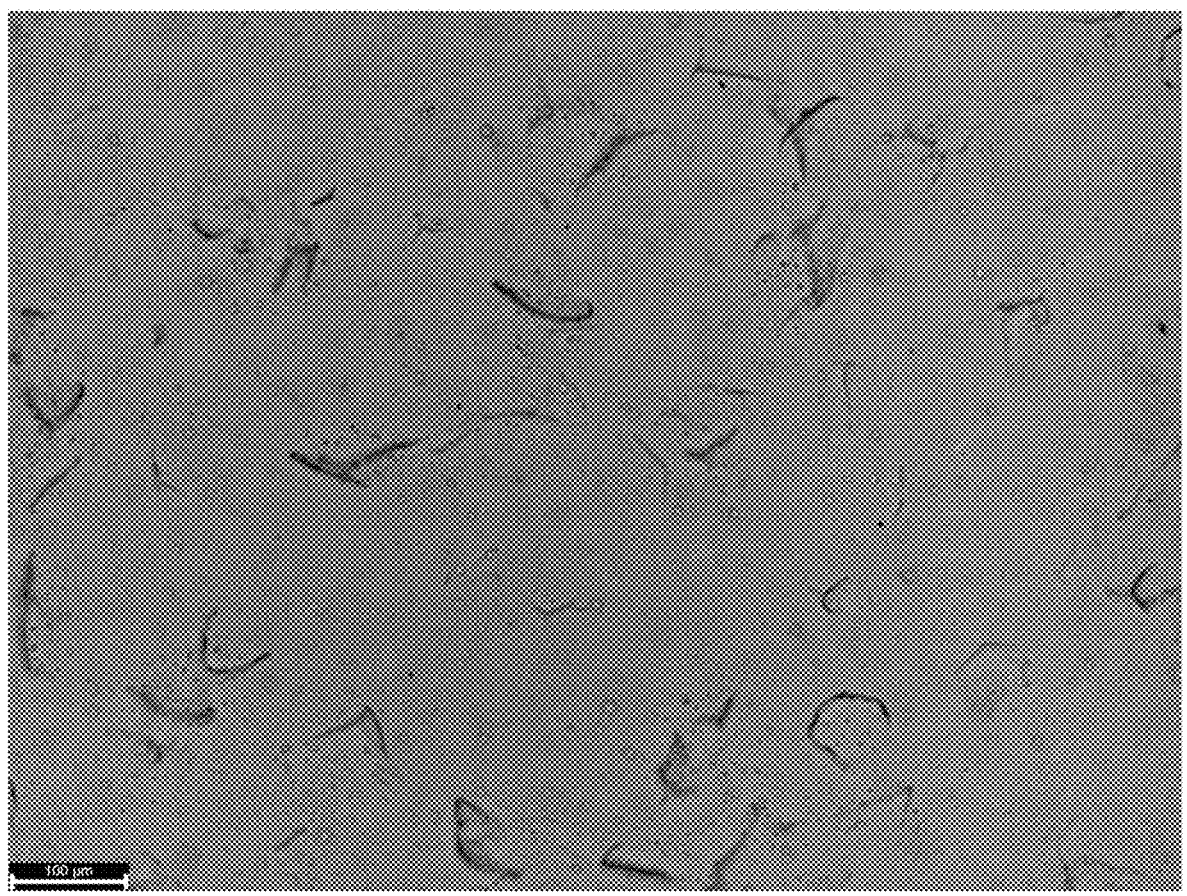
FIG. 4 shows a BrightField image of a skin sample surface after treatment with a third personal care formulation in accordance with aspects of the invention.
Figure 5:
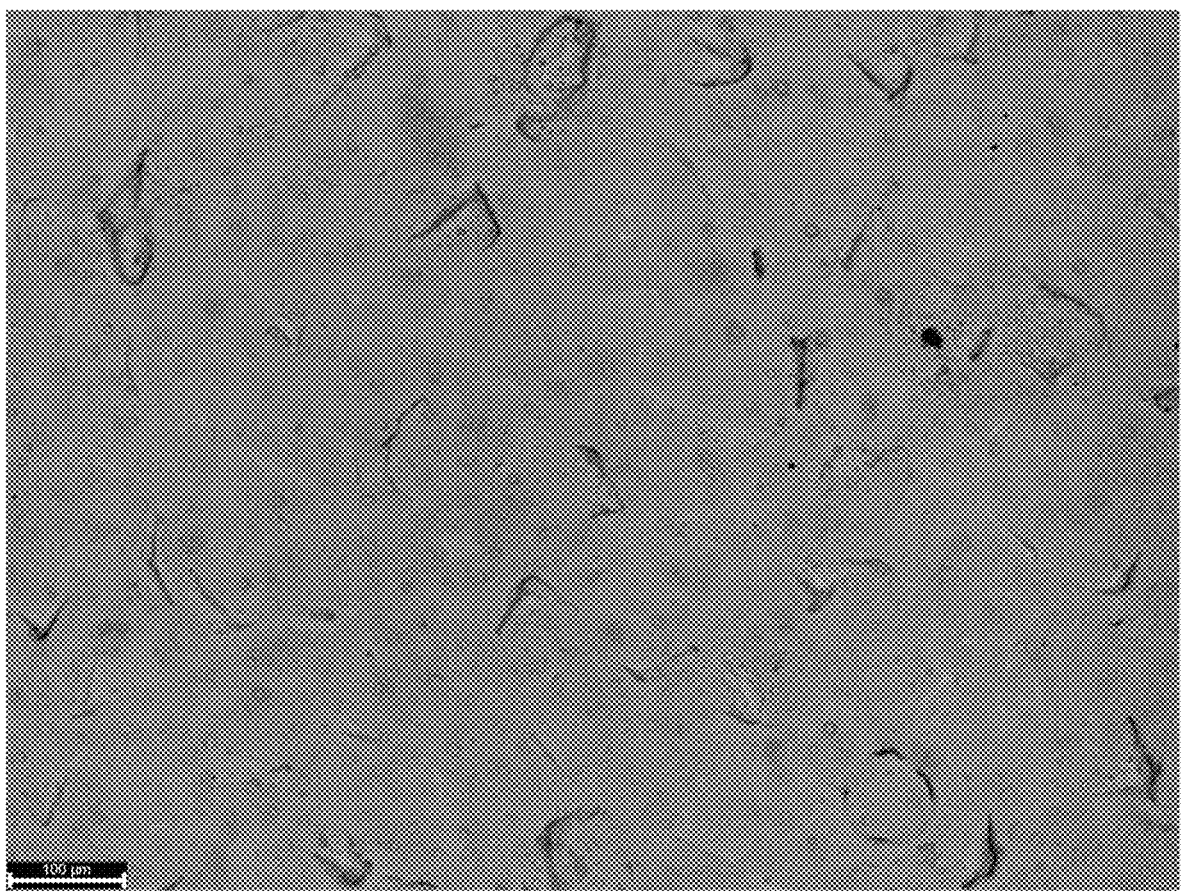
FIG. 5 shows a BrightField image of a skin sample surface after treatment with a fourth personal care formulation according to aspects of the invention.
Figure 6:
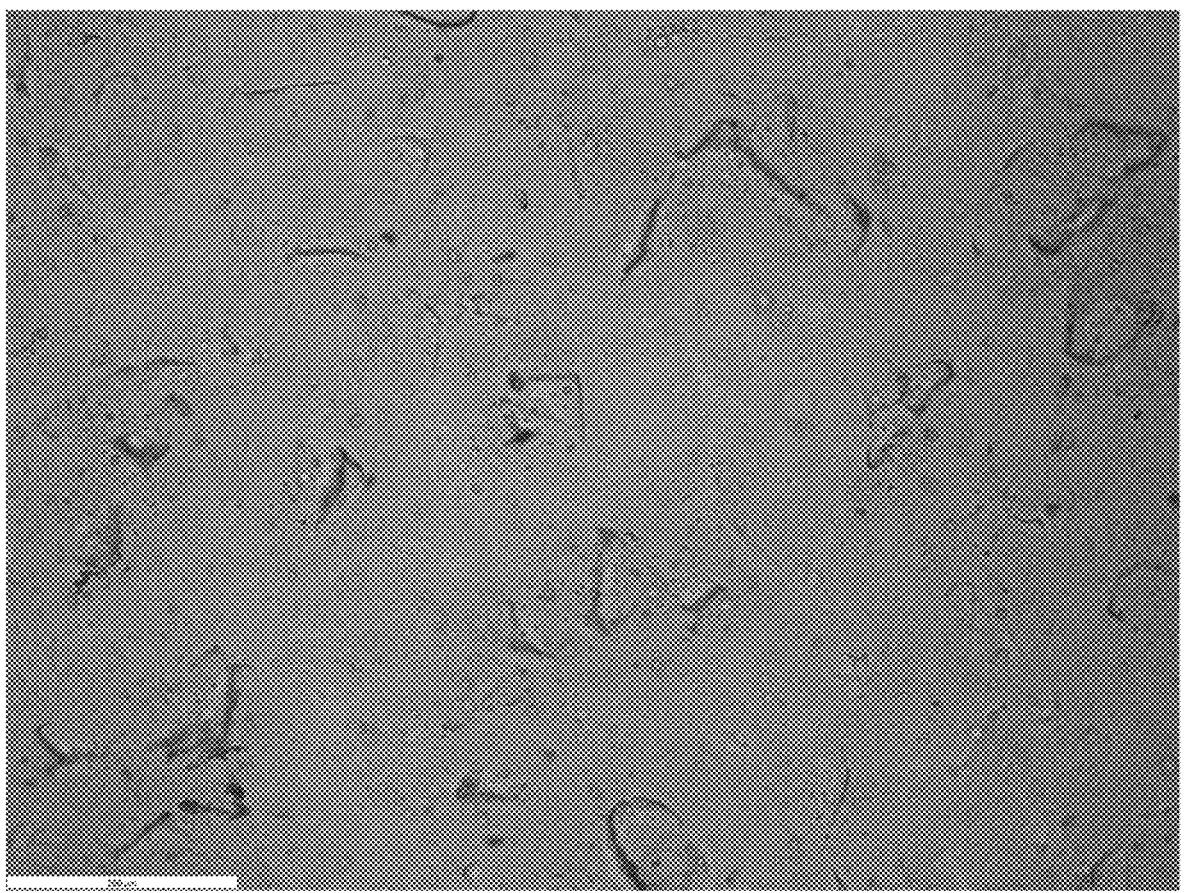
FIG. 6 shows a BrightField image of a skin sample surface after treatment with a fifth personal care formulation in accordance with aspects of the invention.

It is to be understood that the foregoing detailed description of the invention and embodiments, are exemplary and explanatory only and are not restrictive in any way of the claimed invention. As used herein, the use of the plural tense includes the singular tense unless specifically stated otherwise. Similarly, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range. Thus, a range from 1-5, includes specifically 1, 2, 3, 4 and 5, as well as subranges such as 2-5, 3-5, 2-3, 2-4, 1-4, etc. The term "about" when referring to a number means any number within a range of 10% of the number. For example, the phrase "about 2.0 wt. %" refers to a number between and including 1.8 wt. % and 2.2 wt. %.

All references cited herein are hereby incorporated by reference in their entireties. In the event of a conflict in a definition in the present disclosure and that of a cited reference, the present disclosure controls.

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

All components and elements positively set forth in this disclosure can be negatively excluded from the claims. In other words, the personal care formulations of the instant disclosure can be free or essentially free of all components and elements positively recited throughout the instant disclosure. In some instances, the personal care formulation of the present invention may be substantially free of non-incidental amounts of the ingredient(s) or compound(s) described herein. A non-incidental amount of an ingredient or compound is the amount of that ingredient or compound that is added into the personal care formulation by itself. For example, a personal care formulation may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the personal care formulation includes both components (or the formulation includes more than two components that overlap), an overlapping compound does not represent more than one component. For example, certain compounds (e.g., ethanol) may be characterized as both a penetration agent and a carrier. If a particular personal care formulation includes both a penetration agent and a carrier, ethanol will serve only as either a penetration agent or a carrier—not both.

As used herein, reference to a compound comprising several isomers or stereoisomers includes all the isomeric or stereoisomeric forms of that compound. For example when reference is made to lactic acid, it can refer to 1-(+)-lactic acid or d-(−)-lactic acid, or to a mixture thereof. Unless stated otherwise, all percentages of the personal care formulations ingredients, given in this specification, are by weight based on the total personal care formulation weight of 100%.

As used herein, reference to an acid, may include all chemical salts and/or esters of that acid. For example when reference is made to lactic acid, it can refer to a lactate salt or to a lactate ester. Some of the personal care formulations of the invention may comprise ingredients which have several properties, for instance some of the anti-inflammatory ingredients may have soothing properties and/or wound healing properties as well as antipollution properties and antioxidation properties.

As used herein, the term "exfoliating" refers to a cosmetic technique which improves the skin appearance by removing or facilitating the removal of dead skin cells which accumulate on the topmost layer of skin and/or stratum corneum enabling the new layer of skin cells to come to the surface and grow. Exfoliating formulations may comprise gritty solids of varying particle size which provide sensory signals of cleansing when rubbed into the skin. The abrasive nature of these particles suspended in a suitable base provides a smooth after-feel. In some embodiments, the personal care formulations of the present invention are free from gritty solids. In some embodiments, the personal care formulations of the present invention are free of particles with abrasive properties.

As used herein, the term "chemical peel" refers to a skin exfoliant with a low pH from about 0.05 to about 4. Chemical peels are caused by agents that interact with the complex structure of the skin, removing the outer layer to expose the underlying layers. In general, chemical peels dissolve dead cells and may have a watery, gel-like consistency. Chemical peels may comprise fruit enzymes, fruit acids, and/or metal complexes. In some embodiments, however, the personal care formulations of the present invention are free of fruit enzymes, fruit acids, and/or metal complexes. Although chemical peels may comprise retinol, in some embodiments the personal care formulations of the inventions are free from retinol.

The personal care formulations of the invention may be applied on the skin of the human subject. In general, the personal care formulations of the invention may be applied to the face, the back of the hands, the knees, the heels or on the skin of any other parts of the human subject. In some preferable embodiments, the personal care formulations of the invention may be applied to the face.

As used herein, the term "VITRO-SKIN®" refers to a testing substrate which mimics the surface properties of human skin. VITRO-SKIN® is available from IMS. It has been formulated to have topography, pH, critical surface tension, chemical reactivity and ionic strength that is similar to human skin. The effect of the personal care formulations of the invention were evaluated on VITRO-SKIN® samples.

As used herein in the examples and in the Figures, the term "skin samples" refers to VITRO-SKIN® skin samples.

As used herein, the term "topical application" refers to applying or spreading the personal care formulations of the invention on the surface of the skin of the human subject.

As used herein the term "dermatological" refers to skin.

As used herein the term "smoothness of the skin" refers to skin which lacks roughness, without bends and irregularities, and silky to the touch.

As used herein, the terms "surface smoothness" and "surface roughness" refer to the surface texture; they were quantified by the deviations in the direction of the normal vector of a real surface from its ideal form. If these deviations are large, the surface is rough, if they are small, the surface is smooth.

Surface smoothness and surface roughness may be measured with a skidded gage, as in methods including, but not limited to, interferometric optical profilometry or stylus profilometry. The skin surface roughness in the present invention was determined using Atomic Force Microscopy (AFM).

Atomic Force Microscopy is a three-dimensional scanning technique that has <0.2 nm spatial resolution and the ability to measure most types of materials. Surface roughness acquisition via AFM was obtained through the use of a cantilever with a sharp tip at its end that was used to scan the surface. As the tip contacts the surface, the cantilever bends, and the bending is detected using a laser diode and a split photodetector. This bending is indicative of the tip-sample interaction force. When the tip was brought into proximity of a sample surface, forces between the tip and the sample lead to a deflection of the cantilever according to Hooke's law. Surface roughness may be measured in terms of a number of parameters known in the art.

Aspects of the invention are directed to personal care formulation formulated to improve the appearance of skin and/or skin health. In one embodiment, the personal care formulation is a dermatological chemical peel and/or dermatological exfoliating formulation. The inventors discovered that certain combinations of alpha hydroxy acid, beta hydroxy acid, polyhydroxy acid in certain weight ratios provide enhanced benefits to the skin.

In accordance with one aspect of the invention, provided is a personal care formulation comprising an alpha hydroxy acid, a beta hydroxy acid, and a polyhydroxy acid comprising gluconodeltalactone. According to another aspect of the invention, a personal care formulation is provided that comprises an alpha hydroxy acid; a beta hydroxy acid; and polyhydroxy acid, wherein the personal care formulation has a weight ratio of alpha hydroxy acid to polyhydroxy acid is about 5:1 to about 1:4, and wherein the personal care formulation has a weight ratio of beta hydroxy acid to polyhydroxy acid is about 1:1 to about 1:11. In one embodiment, the present invention provides personal care formulations comprising a plurality of ingredients selected from penetration agent(s), alpha hydroxy acid(s), beta hydroxy acid(s), polyhydroxy acid(s), humectants/hydrator(s), soothing agent(s), carrier(s), antioxidant(s), anti-inflammation agent(s), wound healing agent(s), pH adjuster(s), amino acid(s), and a combination of two or more thereof.

In some preferred embodiments, the personal care composition is formulated to have a weight ratio of alpha hydroxy acid to polyhydroxy acid is about 5:1 to about 1:4. For example, the weight ratio of the alpha hydroxy acid to polyhydroxy acid may be about 5:1 to about 1:4, about 5:1 to about 1:3, about 5:1 to about 1:2, about 5:1 to about 1:1; from about 4:1 to about 1:4, about 4:1 to about 1:3, about 4:1 to about 1:2, about 4:1 to about 1:1; from about 3:1 to about 1:4, about 3:1 to about 1:3, about 3:1 to about 1:2, about 3:1 to about 1:1; from about 2:1 to about 1:4, about 2:1 to about 1:3, about 2:1 to about 1:2, or about 2:1 to about 1:1.

Additionally or alternatively, the personal care composition may be formulated to have a weight ratio of beta hydroxy acid to polyhydroxy acid is about 1:1 to about 1:11; about 1:1 to about 1:10, about 1:1 to about 1:9, about 1:1 to about 1:8, about 1:1 to about 1:7, about 1:1 to about 1:6, about 1:1 to about 1:5, about 1:1 to about 1:4, about 1:1 to about 1:3, about 1:1 to about 1:2, or about 1:1.

The personal care compositions may, also or alternatively, be formulated to have a weight ratio of beta hydroxy acid to alpha hydroxy acid is about 1:1 to about 1:11; about 1:1 to about 1:10, about 1:1 to about 1:9, about 1:1 to about 1:8, about 1:1 to about 1:7, about 1:1 to about 1:6, about 1:1 to about 1:5, about 1:1 to about 1:4, about 1:1 to about 1:3, about 1:1 to about 1:2, or about 1:1.

The personal care formulation may comprise one or more penetration agent(s). In general, penetration agents may include, but are not limited to, monoalcohols, ethanol, witch hazel, urea, fatty acids, glycols or combinations thereof. In some embodiments, the penetration agents include monoalcohols, ethanol, propanol, butanol, witch hazel, glycols or combinations thereof. For instance, the penetration agents may include monoalcohol, anhydrous ethyl alcohol, water, and witch hazel. In at least one embodiment, the penetration agents are ethanol and witch hazel.

The personal care formulation may comprise one or more penetration agent(s) in an amount from about 5 by weight to about 99 wt. %, or from about 25 wt. % to about 70 wt. %, or from about 45 to about 55 wt. %, relative to the total weight of the personal care formulation. In some cases, the personal care formulation includes one or more penetration agent(s) in an amount from about 5 to about 90 wt. %, about 5 to about 75 wt. %, about 5 to about 50 wt. %, about 5 to about 25 wt. %, about 5 to about 15 wt. %; from about 25 to about 90 wt. %, about 25 to about 75 wt. %, about 25 to about 50 wt. %, about 25 to about 40 wt. %; from about 40 to about 90 wt. %, about 40 to about 75 wt. %, about 40 to about 60 wt. %; from about 60 to about 90 wt. %, about 60 to about 80 wt. %, about 60 to about 70 wt. %; from about 75 to about 90 wt. %, about 75 to about 85 wt. %; from about 80 to about 90 wt. %, about 85 to about 90 wt. %, or any ranges and subranges thereof, based on the total weight of the personal care formulation. In at least one embodiment, the personal care formulation comprises penetration agent(s) in an amount from about 45 wt. % to about 55 wt. %, based on the total weight of the personal care formulation.

The personal care formulation can include one or more alpha hydroxy acid(s) and/or a salt thereof. For example, the personal care formulation may include one or more one or more alpha hydroxy acid(s), such as those selected from C3 to $C_7$ alpha-hydroxy acid or C4 to C6 alpha-hydroxy acid. In some embodiments, the personal care formulation includes a salt of an alpha-hydroxy acid. The salt of the alpha-hydroxy acid is preferably a sodium salt or a potassium salt. In at least one embodiment, the salt is a sodium salt (i.e., the cation associated with the salt is a sodium). Non-limiting examples of alpha hydroxy acids include but are not limited to, mandelic acid, glycolic acid, citric acid, lactic acid, malic acid, tartaric acid, phytic acid, hydroxycaprylic acid, hydroxycapric acid, glutaric acid, gluconic acid, or a combination of two or more thereof. In some embodiments, the alpha hydroxy acids are citric acid, mandelic acid, glycolic acid, lactic acid or a combination of two or more thereof. In certain instance, the alpha-hydroxy acid is selected from malic acid, tartaric acid, alpha-hydroxy glutaric acid, gluconic acid, a salt thereof, and a combination of two or more thereof. Yet in further instances, the alpha-hydroxy acid or salt thereof is selected from lactic acid, malic acid, and sodium-D-gluconate. In at least one embodiment, the alpha hydroxy acid is lactic acid.

The personal care formulations of the invention may comprise alpha hydroxy acids in an amount from about 2 to about 22 wt. % or from about 7 to about 15 wt. % relative to the total weight of the personal care formulation. For example, the amount of alpha hydroxy acids in the personal are formulations may be from about 2 to about 20 wt. %, about 2 to about 18 wt. %, about 2 to about 16 wt. %, about 2 to about 14 wt. %, about 2 to about 12 wt. %, about 2 to about 10 wt. %; from about 5 to about 22 wt. %, about 5 to about 20 wt. %, about 5 to about 18 wt. %, about 5 to about 16 wt. %, about 5 to about 14 wt. %, about 5 to about 12 wt. %, about 5 to about 10 wt. %; from about 8 to about 22 wt. %, about 8 to about 20 wt. %, about 8 to about 18 wt. %, about 8 to about 16 wt. %, about 8 to about 14 wt. %, about 8 to about 12 wt. %, about 8 to about 10 wt. %; from about 10 to about 22 wt. %, about 10 to about 20 wt. %, about 10 to about 18 wt. %, about 10 to about 16 wt. %, about 10 to about 14 wt. %, about 10 to about 12 wt. %, including any range or subrange thereof, based on the total weight of the personal care formulation. In at least one embodiment, the personal care formulation comprises alpha hydroxy acids in an amount from about 10 to about 15 wt. %, based on the total weight of the personal care formulation.

The personal care formulation typically comprises one or more beta hydroxy acid(s). Non-limiting examples of beta hydroxy acids include salicylic acid, propionic acid, beta-hydroybutyric acid, beta-hydroxy beata-methylbutyric acid, carnitine, and combinations of two or more thereof. The beta hydroxy acids may in some cases be selected from salicylic acid, esters of salicylic acid, sodium salicylate, beta hydroxybutanoic acid, tropic acid, trethocanic acid, beta hydroxyl acids obtained from white willow bark extract and/or wintergreen leaves, and combinations of two or more thereof. In some embodiments, the beta hydroxy acid(s) comprises salicylic acid, sodium salicylate, beta hydroxyl acids of willow bark extract or combinations thereof. In one embodiment, the beta hydroxy acid is salicylic acid.

The personal care formulations of the invention may comprise beta hydroxy acids in an amount from about 0.5 to about 10 wt. %, or from about 1.5 to about 3 wt. %, relative to the total weight formulation. For example, the amount of beta hydroxy acids present in the personal care formulation may be from about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; about 2 to about 10 wt. %, about 2 to about 8 wt. %, about 2 to about 6 wt. %, about 2 to about 5 wt. %, about 2 to about 4 wt. %, about 2 to about 3 wt. %; about 3 to about 10 wt. %, about 3 to about 8 wt. %, about 3 to about 6 wt. %, about 3 to about 5 wt. %, about 3 to about 4 wt. %, including ranges and subranges thereof, based on the total weight of the personal care formulation. In one instance, the personal care formulation comprises beta hydroxy acids from about 1.5 to about 2 wt. %, based on the total weight of the personal care formulation.

Typically, the personal care formulations include one or more polyhydroxy acid(s). The polyhydroxy acids may include, but are not limited to, gluconolactone, gluconic acid, galactose, lactobionic acid, or combinations thereof. In some embodiments, the polyhydroxy acids are gluconolactone, lactobionic acid or combinations thereof. Preferably, the polyhydroxy acid is glucanodeltalactone. Glucanodeltalactone is also referred to as glucono-1,5-lactone or GDL.

The personal care formulations of the invention may comprise polyhydroxy acid(s) in an amount from about 2 to about 20 wt. %, about 7 to about 20 wt. %, or from about 10% to about 15 wt. % by weight, relative to the total weight of the personal care formulation. For example, the polyhydroxy acid(s) may be present in the personal care formulation in an amount from about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 6 wt. %, about 2 to about 4 wt. %; from about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 8 wt. %; from about 8 to about 20 wt. %, about 8 to about 18 wt. %, about 8 to about 16 wt. %, about 8 to about 14 wt. %, about 8 to about 12 wt. %, about 8 to about 10 wt. %; from about 10 to about 20 wt. %, about 10 to about 18 wt. %, about 10 to about 16 wt. %, about 10 to about 14 wt. %, about 10 to about 12 wt. %; from about 12 to about 20 wt. %, about 12 to about 18 wt. %, about 12 to about 16 wt. %, about 12 to about 14 wt. %; from about 14 to about 20 wt. %, about 14 to about 18 wt. %, about 14 to about 16 wt. %; from about 16 to about 20 wt. %, about 16 to about 18 wt. %, including any range or subrange thereof, based on the total weight of the personal care formulation. In at least one instance, the personal care formulation comprises polyhydroxy acid(s) from about 10 to about 15 wt. %, based on the total weight of the personal care formulation.

In general, humectants include, but are not limited to, polyhydric alcohols such as glycerin, butylene glycol, 1,3-propanediol, sorbitol, xylitol or low molecular weight polyethylene glycols (PEGs), polyoxyethylenes or combinations thereof. In some embodiments, the humectant agents are sorbitol (preferably, non-crystal sorbitol), butylene glycol, 1,3-propanediol, glycerin (e.g., vegetable refined glycerin), polyoxyethylene glycol or combinations thereof. In at least one embodiment, the humectants are chosen from glycerin, butylene glycol and 1,3-propanediol. Typically, the humectant is vegetable refined glycerin. Other suitable humectants include, but are not limited to, polyglutamic acid, saccharide isomerate or combinations thereof. In at least one instance, the humectant is saccharide isomerate. Saccharide isomerate can be commercially obtained from, e.g., DSM under the trademark of Pentavitin™.

The personal care formulation of the invention may comprise humectants in an amount from about 1 to about 20 wt. %, or from about 5 to about 10 wt. %, or from about 10 to about 15 wt. %, relative to the total weight of the personal care formulation. For example, the humectants may be present in the personal care formulation in an amount from about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 6 wt. %, about 1 to about 4 wt. %; from about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 6 wt. %, about 2 to about 4 wt. %; from about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 8 wt. %; from about 8 to about 20 wt. %, about 8 to about 18 wt. %, about 8 to about 16 wt. %, about 8 to about 14 wt. %, about 8 to about 12 wt. %, about 8 to about 10 wt. %; from about 10 to about 20 wt. %, about 10 to about 18 wt. %, about 10 to about 16 wt. %, about 10 to about 14 wt. %, about 10 to about 12 wt. %; from about 12 to about 20 wt. %, about 12 to about 18 wt. %, about 12 to about 16 wt. %, about 12 to about 14 wt. %; from about 14 to about 20 wt. %, about 14 to about 18 wt. %, about 14 to about 16 wt. %; from about 16 to about 20 wt. %, about 16 to about 18 wt. %, including any range or subrange thereof, based on the total weight of the personal care formulation. In at least one embodiment, the personal care formulation comprises humectant(s) in an amount from about 1 to about 5 wt. %, based on the total weight of the personal care formulation.

In general, soothing agents include, but are not limited to, natural extracts comprising: centella asiatica extract, polygonum cuspidatum root extract, scutellaria baicalensis root extract, camellia sinensis leaf extract, glycyrrhiza glabra (licorice) root extract, chamomilla recutita (matricaria) flower extract, rosmarinus officinalis (rosemary) leaf extract, tea (camellia sinensis) leaf extract, poria cocos extract, phragmites karka extract, lidocaine, chia seed extract, Rosa centifolia flower extract, aloe vera, allantoin, D-panthenol, turmeric, avocado oil, and lichen extract, or a combination of two or more thereof. Some soothing agents are sold under the names of MultiEx BSASM™ and Syri-Calm CLR™.

The personal care formulation of the invention may, optionally, comprise soothing agent(s) in an amount from about 0 to about 5 wt. %, or from about 0.5 to about 3 wt. %, relative to the total weight of the personal care formulation. For instance, the amount of soothing agent(s) present in the personal are formulation may be from about 0.1 to about 5 wt. %, about 0.1 to about 4 wt. %, about 0.1 to about 3 wt. %, about 0.1 to about 2 wt. %, about 0.1 to about 1 wt. %; from about 0.5 to about 5 wt. %, about 0.5 to about 4 wt. %, about 0.5 to about 3 wt. %, about 0.5 to about 2 wt. %, about 0.5 to about 1 wt. %; from about 1 to about 5 wt. %, about 1 to about 4 wt. %, about 1 to about 3 wt. %, about 1 to about 2 wt. %; from about 2 to about 5 wt. %, about 2 to about 4 wt. %, about 2 to about 3 wt. %; from about 3 to about 5 wt. %, about 3 to about 4 wt. %, or any range or subrange thereof, based on the total weight of the personal care formulation.

The personal care formulation may include one or more carrier(s). In general, carriers include but are not limited to, water or alcohols (e.g., ethanol, isopropanol or mixtures thereof). In at least one embodiment, the carrier comprises water. The amount of carrier present in the personal care formulation may vary, e.g., from about 5 to about 90 wt. %, based on the total weight of the personal care formulation. In some cases, the personal care formulation includes one or more carrier(s) in an amount from about 5 to about 75 wt. %, about 5 to about 50 wt. %, about 5 to about 25 wt. %, about 5 to about 15 wt. %; from about 25 to about 90 wt. %, about 25 to about 75 wt. %, about 25 to about 50 wt. %, about 25 to about 40 wt. %; from about 40 to about 90 wt. %, about 40 to about 75 wt. %, about 40 to about 60 wt. %; from about 60 to about 90 wt. %, about 60 to about 80 wt. %, about 60 to about 70 wt. %; from about 75 to about 90 wt. %, about 75 to about 85 wt. %; from about 80 to about 90 wt. %, about 85 to about 90 wt. %, or any ranges and subranges thereof, based on the total weight of the personal care formulation.

In some embodiments, the personal care formulation comprises one or more antioxidant(s). Examples of antioxidants include, but are not limited to, camellia japonica extract, quercetin or combinations thereof. Quercetin is commercially available under the trademark of Quercevita™. Typically the antioxidant is Camellia Japonica extract. Camellia Japonica extract is sold under the name of RedSnow®. The personal care formulation of the invention may comprise one or more antioxidant(s) from about 0 to about 5 wt. %, or from about 0.5 to about 3 wt. %, relative to the total weight of the personal care formulation. In some cases, the amount of antioxidant(s) present in the personal are formulation may be from about 0.1 to about 5 wt. %, about 0.1 to about 4 wt. %, about 0.1 to about 3 wt. %, about 0.1 to about 2 wt. %, about 0.1 to about 1 wt. %; from about 0.5 to about 5 wt. %, about 0.5 to about 4 wt. %, about 0.5 to about 3 wt. %, about 0.5 to about 2 wt. %, about 0.5 to about 1 wt. %; from about 1 to about 5 wt. %, about 1 to about 4 wt. %, about 1 to about 3 wt. %, about 1 to about 2 wt. %; from about 2 to about 5 wt. %, about 2 to about 4 wt. %, about 2 to about 3 wt. %; from about 3 to about 5 wt. %, about 3 to about 4 wt. %, or any range or subrange thereof, based on the total weight of the personal care formulation.

In general, wound healing agents include but are not limited to, triterpenes, triterpenoids, oleanolic acid, maslinic acid, asiaticoside or combinations thereof. In some embodiments, the wound healing agents include asiaticoside and oleanolic acid or a combination of two or more thereof. Typically, the wound healing agent is asiaticoside. Asiaticoside has antipollution, anti-inflammatory and/or antioxidation properties. The personal care formulation of the invention may comprise one or more wound healing agent(s) from about 0 to about 5 wt. %, or from about 0.5 to about 3 wt. %, relative to the total weight of the personal care formulation. In some cases, the amount of wound healing agent (s) present in the personal are formulation may be from about 0.1 to about 5 wt. %, about 0.1 to about 4 wt. %, about 0.1 to about 3 wt. %, about 0.1 to about 2 wt. %, about 0.1 to about 1 wt. %; from about 0.5 to about 5 wt. %, about 0.5 to about 4 wt. %, about 0.5 to about 3 wt. %, about 0.5 to about 2 wt. %, about 0.5 to about 1 wt. %; from about 1 to about 5 wt. %, about 1 to about 4 wt. %, about 1 to about 3 wt. %, about 1 to about 2 wt. %; from about 2 to about 5 wt. %, about 2 to about 4 wt. %, about 2 to about 3 wt. %; from about 3 to about 5 wt. %, about 3 to about 4 wt. %, or any range or subrange thereof, based on the total weight of the personal care formulation.

The personal care formulation in some instances comprises one or more amino acid(s). In general, amino acids include, but are not limited to, arginine, methionine, taurine, leucine, glycine, valine, lysine, alanine, cysteine, histidine, leucine, proline, serine, tyrosine or a combination of two or more thereof. In some embodiments, the amino acids include arginine, taurine, glycine, histidine, methionine, lysine, proline, leucine or combinations thereof. Typically, the amino acid is arginine. The personal care formulations of the invention may comprise amino acids from about 0.5 by weight to about 10wt. %, or from about to 1 to about 2 wt. %, or from about 2 to about 4 wt. %, or from about 4 to about 6 wt. %, or from about 6 to about 8 wt. %, or from about 8 to about 10 wt. %, relative to the total weight of the personal care formulation. In some embodiments, the personal care formulation comprises one or more amino acid in an amount from about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; from about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; from about 2 to about 10 wt. %, about 2 to about 8 wt. %, about 2 to about 6 wt. %, about 2 to about 5 wt. %, about 2 to about 4 wt. %; from about 4 to about 10 wt. %, about 4 to about 8 wt. %, about 4 to about 6 wt. %; from about 6 to about 10 wt. %, about 6 to about 8 wt. %; from about 8 to about 10 wt. %, or any range or subrange thereof, based on the total weight of the personal care formulation. In at least one embodiment, the personal care formulations of the invention comprise wound healing agents from about 1 to about 2 wt., based on the total weight of the personal care composition.

In one embodiment, the present invention provides a personal care formulation which is an exfoliating formulation, comprising penetration agents, alpha hydroxy acids, beta hydroxy acids, polyhydroxy acids, humectants, soothing agents, anti-inflammatory, carriers, pH adjusters, antioxidants, wound healing agents, amino acids or combinations thereof. In one embodiment, the present invention provides a personal care formulation, which is a chemical peel, and comprises one or more of penetration agents, alpha hydroxy acids, beta hydroxy acids, polyhydroxy acids, humectants, soothing agents, anti-inflammatory, carriers, pH adjusters, antioxidants, wound healing agents, amino acids or combination of two or more thereof.

In one embodiment, the present invention provides a personal care formulation comprising: penetration agents, wherein the penetration agents include denatured alcohol, anhydrous ethyl alcohol, water, witch hazel, urea, fatty acids, glycols or combinations thereof; alpha hydroxy acids, wherein the alpha hydroxy acids include citric acid, mandelic acid, glycolic acid, lactic acid, malic acid, phytic acid, hydroxycaprylic acid, hydroxycapric acid, tartaric acid or combinations thereof; beta hydroxy acids, wherein the beta hydroxy acids include salicylic acid, esters of salicylic acid, sodium salicylate, white willow bark extract, wintergreen leaves, beta hydroxybutanoic acid, tropic acid, trethocanic acid or combinations thereof; polyhydroxy acids, wherein the polyhydroxy acids include gluconolactone, gluconic acid, galactose, lactobionic acid or combinations thereof; humectants, wherein the humectants include polyhydric alcohols such as vegetable refined glycerin, butylene glycol, 1,3-propanediol, non crystal sorbitol, xylitol or low molecular weight polyethylene glycols, polyoxyethylenes, polyglutamic acid, saccharide isomerate or combinations of two or more thereof; soothing agents, wherein the soothing agents, include natural extracts comprising: centella asiatica extract, polygonum cuspidatum root extract, scutellaria baicalensis root extract, camellia sinensis leaf extract, glycyrrhiza glabra root extract, chamomilla recutita flower extract, rosmarinus officinalis leaf extract, tea leaf extract, poria cocos extract, phragmites karka extract or combinations thereof; antioxidants, wherein the antioxidants, include camellia japonica extract, quercetin or combinations thereof; wound healing agents, wherein the wound healing agents include triterpenes, triterpenoids, oleanolic acid, maslinic acid, asiaticoside or combinations thereof; amino acids, wherein the amino acids include arginine, methionine, taurine, leucine, glycine, valine, lysine, alanine, cysteine, histidine, leucine, proline, serine, tyrosine or combinations thereof.

In one embodiment, the present invention provides a personal care formulation comprising: penetration agents, wherein the penetration agents include denatured alcohol, anhydrous ethyl alcohol, witch hazel, or combinations thereof; alpha hydroxy acids, wherein the alpha hydroxy acids include citric acid, glycolic acid, lactic acid or combinations thereof; beta hydroxy acids, wherein the beta hydroxy acids include salicylic acid, sodium salicylate, willow extract, or combinations thereof, polyhydroxy acids, wherein the polyhydroxy acids include gluconolactone or lactobionic acid, or combinations thereof; humectants, wherein the humectants include non-crystal sorbitol, butylene glycol,1,3-propanediol, vegetable refined glycerin or polyoxyethylene glycol polyglutamic acid, saccharide isomerate, or combination thereof; soothing agents, wherein the soothing agents, include natural extracts comprising: centella asiatica extract, polygonum cuspidatum root extract, scutellaria baicalensis root extract, camellia sinensis leaf extract, glycyrrhiza glabra root extract, chamomilla recutita flower extract, rosmarinus officinalis leaf extract, tea leaf extract, poria cocos extract, phragmites karka extract, or combinations thereof; antioxidants, wherein the antioxidants include camellia japonica extract, quercetin or combinations thereof; wound healing agents, wherein the wound healing agents include asiaticoside, oleanolic acid, or combinations thereof; amino acids, wherein the amino acids include arginine, taurine, glycine, histidine, methionine, lysine, proline, leucine or combinations thereof.

In one embodiment, the present invention provides a personal care formulation comprising: penetration agents, wherein the penetration agents include anhydrous ethyl alcohol, and witch hazel; alpha hydroxy acids, wherein the alpha hydroxy acids include lactic acid; beta hydroxy acids, wherein the beta hydroxy acids include salicylic acid; polyhydroxy acids, wherein the polyhydroxy acids include gluconolactone; humectants, wherein the humectants include butylene glycol,1,3-propanediol and vegetable refined glycerin, saccharide isomerate; soothing agents, wherein the soothing agents, include natural extracts comprising: centella asiatica extract, polygonum cuspidatum root extract, scutellaria baicalensis root extract, camellia sinensis leaf extract, glycyrrhiza glabra root extract, chamomilla recutita flower extract, rosmarinus officinalis leaf extract, tea leaf extract, poria cocos extract, phragmites karka extract, or combinations thereof; antioxidants, wherein the antioxidants include camellia japonica extract, quercetin, or combinations thereof; wound healing agents, wherein the wound healing agents include asiaticoside; amino acids, wherein the amino acids include arginine. In one embodiment, the present invention provides a personal care formulation comprising: anhydrous ethyl alcohol, witch hazel, salicylic acid, butylene glycol,1,3-propanediol,vegetable refined glycerin, saccharide isomerate, gluconolactone, lactic acid, demineralized water, centella asiatica extract, polygonum cuspidatum root extract, scutellaria baicalensis root extract, camellia sinensis leaf extract, glycyrrhiza glabra root extract, chamomilla recutita flower extract, rosmarinus officinalis leaf extract, tea leaf extract, poria cocos extract, phragmites karka, camellia japonica extract, quercetin, asiaticoside, arginine, and a combination of two or more thereof.

In one embodiment, the present invention provides a personal care formulation comprising: anhydrous ethyl alcohol, witch hazel, salicylic acid, butylene glycol,1,3-propanediol, vegetable refined glycerin, saccharide isomerate, gluconolactone, lactic acid, demineralized water, centella asiatica extract, polygonum cuspidatum root extract, scutellaria baicalensis root extract, camellia sinensis leaf extract, glycyrrhiza glabra root extract, chamomilla recutita flower extract, rosmarinus officinalis leaf extract, tea leaf extract, poria cocos extract, phragmites karka, camellia japonica extract, asiaticoside, and arginine.

In one embodiment, the present invention provides a personal care formulation comprising: anhydrous ethyl alcohol, witch hazel, salicylic acid, vegetable refined glycerin, saccharide isomerate, gluconolactone, lactic acid, demineralized water, asiaticoside and arginine. In one embodiment, the present invention provides a personal care formulation comprising: anhydrous ethyl alcohol, witch hazel, salicylic acid, vegetable refined glycerin, saccharide isomerate, gluconolactone, lactic acid, demineralized water, centella asiatica extract, polygonum cuspidatum root extract, scutellaria baicalensis root extract, camellia sinensis leaf extract, glycyrrhiza glabra root extract, chamomilla recutita flower extract, rosmarinus officinalis leaf extract, tea leaf extract, poria cocos extract, phragmites karka, camellia japonica extract, asiaticoside and arginine.

In one embodiment, the present invention provides a personal care formulation comprising: anhydrous ethyl alcohol, witch hazel, salicylic acid, vegetable refined glycerin, polyglutamic acid, gluconolactone, lactic acid, mandelic acid and demineralized water.

The pH of the personal care formulations is an important factor in the availability of the acid and the stability of the formulation. A low pH is necessary in order to enhance the penetration of the acid into the stratum corneum. Acids, bases, and buffers may be used to adjust the pH of the formulations of the invention. pH adjusters include but are not limited to, ammonia, sodium carbonate, sodium hydroxide, triethanolamine, hydrochloric acid, phosphoric acid, sodium hydrogen phosphate, sodium dihydrogen phosphate, citric acid, and the like. Typically, the personal care formulations of the invention comprise sodium hydroxide as pH adjuster. The personal care formulations of the present invention have a pH comprised from about 2.80 to about 4.10, or from about 2.80 to about 2.90, or from about 2.90 to about 3.00, or from about 3.00 to about 3.10, or from about 3.10 to about 3.20, or from about 3.20 to about 3.30, or from about 3.30 to about 3.40, or from about 3.40 to about 3.50, or from about 3.60 to about 3.70, or from about 3.70 to about 3.80, or from about 3.80 to about 3.90, or from about 3.90 to about 4.00, or from about 4.00 to about 4.10.

In some embodiments, provided are personal care formulations having a composition comprising one or more components and/or ingredients in accordance with Table 1, below. The personal care formulation may have a pH of about 2.8 to about 6.5, about 2.8 to about 5.1, or about 2.8 to about 4.1.

TABLE 1

| | INGREDIENTS | WEIGHT (%) |
|---|---|---|
| 1 | Penetration aids<br>(e.g. denatured alcohol, witch hazel, urea, fatty acids, glycols) | 15-99 |
| 2 | Alpha hydroxy acids<br>(e.g. citric acid, glycolic acid, mandelic acid, lactic acid, malic acid, tartaric acid) | 7-22 |
| 3 | Beta hydroxy acids<br>(e.g. salicylic acid, esters of salicylic acid, sodium salicylate, white willow bark extract, wintergreen leaves, beta hydroxybutanoic acid, tropic acid, trethocanic acid) | 1-5 |

TABLE 1-continued

| | INGREDIENTS | WEIGHT (%) |
|---|---|---|
| 4 | Polyhydroxy acids<br>(e.g. gluconolactone, galactose, and lactobionic acid) | 7-22 |
| 5 | Humectants<br>(e.g. polyhydric alcohols such as vegetable refined glycerin, butylene glycol, 1,3-propanediol, non crystal sorbitol, xylitol or low molecular weight polyethylene glycols, polyoxyethylenes, polyglutamic acid, saccharide isomerate) | 1-20 |
| 6 | Soothing agents<br>(e.g. centella asiatica extract, polygonum cuspidatum root extract, scutellaria baicalensis root extract, camellia sinensis leaf extract, glycyrrhiza glabra root extract, chamomilla recutita flower extract, rosmarinus officinalis leaf extract, tea leaf extract, poria cocos extract, phragmites karka extract) | up to 5 |
| 7 | Antioxidants<br>(e.g. camellia japonica extract, quercetin) | up to 5.00 |
| 8 | Wound healing agents<br>(e.g. triterpenes, triterpenoids, oleanolic acid, maslinic acid, asiaticoside) | up to 5.00 |
| 9 | Amino acids<br>(e.g. arginine, taurine, glycine, valine, lysine, alanine, cysteine, histidine, leucine, proline, serine, tyrosine) | 1-10 |
| 10 | D.I. Water | q.s. * 100 |

"*" quantum sufficient (as much as is sufficient)

In one embodiment, the present invention provides a method of making the personal care formulations of the invention.

In one embodiment, the present invention provides personal care formulations useful in reducing fine wrinkles and lines, reducing pore size, exfoliating the skin, eliminating acne, toning the skin, enhancing the skin's radiance, and providing softer, smoother skin with a more uniform appearance.

In one embodiment, the present invention provides a method to treat skin aging and improve the skin's appearance, by treating the skin with a personal care formulation of the invention.

In one embodiment, the present invention provides a method to even skin tone, even hyperpigmentation, clear acne, improve the appearance of aging skin and make dull complexions glow, by treating the skin with a personal care formulation of the invention.

In one embodiment, the present invention provides a method to increase the skin's cell turnover rate by stimulating the epidermis to produce fresh skin, bringing new skin cells to the surface, reducing signs of fine lines, wrinkles, dark spots and clearing breakouts by treating the skin with a personal care formulation of the invention.

In one embodiment, the present invention provides a method to treat hyperpigmented and photoaged skin due to sun damage, by treating the skin with a personal care formulation of the invention.

In one embodiment, the present invention provides a method to treat dermatological disorders including dry skin, acne, dandruff, keratosis, age spots, wrinkles and disturbed keratinization, by treating the skin with a personal care formulation of the invention.

In one embodiment, the present invention provides a method for treating the skin, comprising applying to the skin a personal care formulation, wherein the pH of the formulation is between about 2.8 and about 4.1; and wherein the personal care formulation comprises the ingredients according to Table 1.

The personal care formulations of the present invention may be formulated as oil-in-water, where oil is in the dispersed phase, and water is the dispersion medium, or water-in-oil, where the reverse is true, emulsions, comprising emulsifiers, gels, liquids, creams, toners, pastes, skin lotions, serums. The personal care formulations of the present invention may be formulated as a solution, suspension, emulsion, paste, gel, cream, sheet mask, lotion, powder, soap, surfactant-containing cleansing, oil, powder foundation, emulsion foundation, wax foundation, or a spray. The personal care formulations of the present invention may be applied with muslin cloths, sponges, brushes, gloves, pads, paper, single-use pads, single use paper masks, cotton and microdermabrasion. The personal care formulations of the present invention may be formulated, packaged and provided in a kit format, comprising one or more of the chemical peel formulations, along with instructions for their use. Such kits may optionally include a means for estimating or measuring the pH of skin before and after treatment with one or more components of the kit. If a means for estimating or measuring the pH of skin before and after treatment is included, it can further require the inclusion of pH testing reagents, indicator (litmus) papers, or a non-invasive, or electronic means. The kit may comprise a post-peel mask for soothing the effect of the chemical peel.

The personal care formulations of the invention may optionally comprise preservative systems, wherein the preservative systems may include, but are not limited to, imidazolidinyl urea, diazolidinyl urea, phenoxyethanol, methylparaben, ethylparaben, and propylparaben.

The personal care formulations of the invention may be used by non-professional subjects such as consumers for at-home treatment, the formulations being capable of providing an improvement of the skin comparable to results obtainable only by professionals using higher concentrations of acid.

The personal care formulations of the invention may be formulated as one step treatment or as multiple step treatment to be used sequentially on the skin of the human subject.

The personal care formulations of the invention may optionally comprise mineral acids, wherein the mineral acids, include, but are not limited to, trichloracetic acid.

The personal care formulations of the invention may optionally comprise metals wherein the metals, include, but are not limited to, selenium, zinc, copper, and silicon.

The personal care formulations of the invention may optionally comprise cooling agents, wherein the cooling agents, include, but are not limited to mint oil, cyclic a-keto enamines, aloe vera, chamomile, green tea, peppermint, lemon, eucalyptus and rose.

The personal care formulations of the invention may optionally comprise vitamins and vitamin derivatives, wherein the vitamins may include, but are not limited to, Vitamin A, retinyl acetate, retinyl palmitate, Vitamin C, ascorbic acid, ascorbyl palmitate, magnesium ascorbyl palmitate, magnesium ascorbyl phosphate, Vitamin E, and tocopherol.

The personal care formulations of the invention may optionally comprise botanicals, wherein the botanicals include, but are not limited to, carotenoids, polyphenols, apigenin (flavonoid occurring in numerous herbs, fruits and vegetables), quercetin (flavonol found in onion skin and apple peel), curcumin (from turmeric rhizome), silymarin (extract of flavonolignans from milk thistle), isoflavones, genistein (isoflavone from soybeans), proanthocyanidins (from seeds of grapes), and resveratrol (polyphenol found in grapes, peanuts, fruits, red wine and mulberries).

Additional or alternative humectants that may optionally be present in the personal care formulations include, but are not limited to, glucuronic acid, N-acetyl-glucosamine, hyaluronic acid of different molecular weights, different salts of hyaluronic acid (acetylated hyaluronic acid, sodium acetylated hyaluronate, sodium hyaluronate, potassium hyaluronate).

The personal care formulations of the invention may optionally comprise fatty acids, wherein the fatty acids include, but are not limited to, polyunsaturated omega-3, omega-6 fatty acids, alpha-linolenic acid (ALA), linoleic acid (LA), gamma linolenic (GLA) acid, docosahexanaenoic acid (DHA), eicosapentaenoic acid (EPA), arachidonic acid (AA), cholesterol, ceramides.

The personal care formulations of the invention may optionally comprise antimicrobials, wherein the antimicrobials may include, but are not limited to, benzoyl peroxide, erythromycin, tetracycline, triclosan, azelaic acid, clindamycin, chlorhexidine, tetracycline, neomycin, miconazole, clotrimazole.

The personal care formulations of the invention may optionally comprise oils, wherein the oils include, but are not limited to, borage oil, evening primrose oil, blackcurrant seed oil, hemp oil, baobab oil, neem oil, black cumin oil, coconut oil, se buckthorn oil, green coffee oil, wheat germ oil, barbary fig oil, argan oil, flaxseed oil.

The personal care formulations of the invention may optionally comprise aesthetic components such as fragrances, pigments, colorants, essential oils, skin sensates, and astringents. Such aesthetic components include, but are not limited to, clove oil, menthol, camphor, eucalyptus oil, eugenol, menthyl lactate, bisabolol, green tea extract.

The personal care formulations of the invention may optionally comprise absorbents, antifoaming agents, antimicrobial agents, binders, biological additives, chelating agents denaturants, external analgesics, steroidal anti-inflammatory drugs, reducing agents, skin bleaching agents, skin protectants, solubilizing agents, solvents, and thickening agents.

The personal care formulations of the invention may optionally comprise skin bleaching agents, wherein the skin bleaching agents include, but are not limited to, hydroquinone, kojic acid, sodium metabisulfite, licorice extract, resorcinol, phenylethyl resorcinol.

The personal care formulations of the invention may optionally comprise peptides, wherein the peptides, known as glycyl-L-histidyl-L-lysine (GHK), bind easily to copper enzymes, forming GHK-Cu.

The personal care formulations of the invention may optionally comprise bioactive compounds naturally produced by marine algae, wherein these bioactive compounds are seaweed crystals, which penetrate the epidermal layer of the skin, and reduce acne inflammation and oil production.

The personal care formulations of the invention may optionally comprise surfactants and/or emulsifying agents, wherein the surfactants and/or emulsifying agents include but are not limited to, ceteareths, ceteths, cetyl alcohol, deceths, dodoxynols, glyceryl palmitate, glyceryl stearate, laneths, myreths, nonoxynols, octoxynols, oleths, PEG-castor oil, poloxamers, poloxamines, polysorbates, ammonium laureth sulfate and sodium laureth sulfate, octoxynol-9 and polysorbate-20.

EXAMPLES

The following examples are for illustrative purposes only and are not intended, nor should they be construed as limiting the invention in any manner. Those skilled in the art will appreciate that variations and modifications of the following examples may be made without exceeding the spirit or scope of the invention.

Example 1

General Procedure For Making An Exemplary Personal Care Formulations

A mixture of demineralized water and penetration agents was stirred at room temperature, in a vessel. The hydroxy acids and the amino acid were added. The mixture was continuously stirred until complete dissolution of the added materials. Once the solution became homogeneous, the humectants were added. If the personal care formulation comprised soothing agents, wound healing agents, humectants/hydrators, antioxidants and/or anti-inflammatory agents, they were added at this stage. The final pH of the formulations was adjusted between 3 and 3.5 with sodium hydroxide.

Table 2, provided on the following page, shows non-limiting ranges for representative ingredients of non-limiting embodiments of the personal care formulations.

TABLE 2

| | INGREDIENT | WEIGHT (%) |
|---|---|---|
| 1 | Penetration aids (e.g. anhydrous ethyl alcohol, witch hazel) | 45-55 |
| 2 | Alpha hydroxy acids (e.g. citric acid, glycolic acid, mandelic acid, lactic acid, malic acid, tartaric acid,) | 10-15 |
| 3 | Beta hydroxy acids (e.g. salicylic acid, esters of salicylic acid, sodium salicylate, white willow bark extract, wintergreen leaves, beta hydroxybutanoic acid, tropic acid, trethocanic acid) | 1.5-2 |
| 4 | Polyhydroxy acids (e.g. gluconolactone, gluconic acid) | 10-15 |
| 5 | Humectants (e.g., glycerin, butylene glycol, 1,3-propanediol, polyglutamic acid, saccharide isomerate) | 1-5 |
| 6 | Soothing agents/anti-inflammatory agents (e.g. centella asiatica extract, polygonum cuspidatum root extract, scutellaria baicalensis root extract, camellia sinensis leaf extract, glycyrrhiza glabra root extract, chamomilla recutita flower extract, rosmarinus officinalis leaf extract, tea leaf extract, poria cocos extract, phragmites karka extract) | 0-5 |
| 7 | Antioxidants (e.g. camellia japonica extract, quercetin) | 0-5 |
| 8 | Wound healing agents (e.g. triterpenes, triterpenoids, oleanolic acid, maslinic acid, asiaticoside) | 0-0.5 |
| 9 | Amino acids (e.g. arginine, taurine, glycine, valine, lysine, alanine, cysteine, histidine, leucine, proline, serine, tyrosine) | 1-2 |
| 10 | Demineralized water | q.s. 100 |

Example 2

Examples Of Personal Care Formulations

In order to evaluate the personal care formulations, several formulations were prepared according to the general procedure according to Example 1. Different combinations of active ingredients were present in these formulations, as tabulated in Table 3.

TABLE 3

| Formulation | AHA[1] [wt. %] | BHA[2] [wt. %] | PHA [wt. %] | Amino Acid[5] [wt. %] | Soothing antioxidants, wound healing, anti-inflammatory agents [wt. %] |
|---|---|---|---|---|---|
| A | 10 | 2 | $10^3$ | 0 | 0 |
| B | 15 | 2 | $10^3$ | 0 | 0 |
| C | 15 | 2 | $10^3$ | 1.07 | 0 |
| D | 15 | 2 | $10^3$ | 1.07 | 3.2 |
| E | 15 | 2 | $10^4$ | 1.07 | 3.2 |

[1]lactic acid;
[2]Salicylic acid;
[3]GDL;
[4]gluconic acid;
[5]arginine;
Formulations A, B, C, D and E were evaluated on VITRO-SKIN® samples as described below.

Example 3

Sample Preparation For Light Microscopy And Atomic Force Microscopy

For Light Microscopy (LM) and Atomic Force Microscopy (AFM), 1cm×1cm pieces of skin samples (VITRO-SKIN®) were cleaned with hexanes to remove residual oils from the manufacturing process, and rinsed 3 times with demineralized water. The skin samples were hydrated for 30 minutes in demineralized water in an attempt to mimic physiological conditions prior to treatment. The cleaned and hydrated samples were either placed on a standard microscope slide with a coverslip for LM evaluation or mounted on a magnetic disk for AFM evaluation. The samples prepared according to the above description were utilized as the baselines.

The treatment for all the skin samples was identical. The personal care Formulations A, B, C, D and E were tested independently on skin samples. Each skin sample was dipped into one of the personal care formulations to be tested, Formulations A, B, C, D or E, for 15 seconds and allowed to treat for 10 minutes prior to imaging. The skin samples were covered with coverslips to prevent dehydration.

Example 4

Light Microscopy Evaluation

Light microscopy determined the effect on the smoothness on the surface of each skin sample, after the treatment with the personal care formulations of Example 2. Light Microscopy provided a qualitative view of the personal care Formulations A, B, C, D or E, effect on the skin sample. For a microscopic view, each sample was imaged using conventional transmission optical microscopy (Leica DMI6000b). The samples were placed on stage and imaged using Bright-Field Mode with10×-40× objectives; the images were digitally recorded. FIG. 1 shows a BrightField image of the surface of the skin sample after hydration and before any treatment, it was used as the baseline. The taller features on the skin surface are darker and the more flat areas are indicative of the surface which was in the focal plane. FIGS. 2, 3, 4, 5 and 6, show the surface of the skin samples after treatment with the respective personal care Formulations A, B, C, D or E, as visualized through BrightField microscopy (10× objective). After treatment with personal care Formulations A, B, C, D or E, the skin samples show a qualitative smoothing effect.

Example 5

Atomic Force Microscopy Evaluation

Atomic Force Microscopy determined the quantitative roughness of the surface of the skin samples. AFM allowed for roughness quantification with little/no sample destruction. After treatment with Formulations A, B, C, D or E, the skin samples were imaged after being placed on a magnetic disk and mounted on the J-scanner of the Multimode 8 with a Nanoscope V controller (Bruker). The skin samples were imaged using PeakForce-Quantitative Nanomechanical Mapping (PeakForce QNM) in air at a scan rate of 0.5-1.5 Hz. The AFM probe utilized in all imaging analysis was the POINTPROBE-PLUS Silicon-SPM Sensor by Nanosensors. The characteristics of the implored probe include a resonant frequency of 45-115 kHz, a spring constant of 0.5-9.5 N/m, and nominal radius of <10 nm. For each skin sample treated with a personal care Formulation A, B, C, D or E, at least three different areas were tested. Prior to imaging and analysis, the deflection sensitivity was calibrated on a sapphire substrate as well as on polydimethylsiloxane to validate calibration. Although the spring constant "k" of the probe was known, "k" was calibrated using the thermal tune method (Lorentzian air) and fit to achieve a value within 10% of the given value. Images were acquired from 30 nm down to 3.5 nm scales, aspect ratio of 1.00, and either 256 or 512 data points/line. Once images were obtained, processing was done using the NanoScope Analysis Software v. 1.5 (Bruker). All plane-fitting and image processing were consistent through all images analyzed (2nd Plane-Fit and 2nd order flatten). Atomic force microscope images showcase the height channel which allows for the visualization of changes in surface topography before treatment and after treatment with Formulations A, B, C, D and E, respectively. The z-scale bar was kept constant for all images from −50 nm to +50 nm and was essentially showing the color gradient of high/tall features vs. low/short features. From the color gradient utilized for these images, the more white the features, the higher they are (approaching 50 nm) and the more black/dark gray features, the lower they are (<50 nm).

Figure 7:
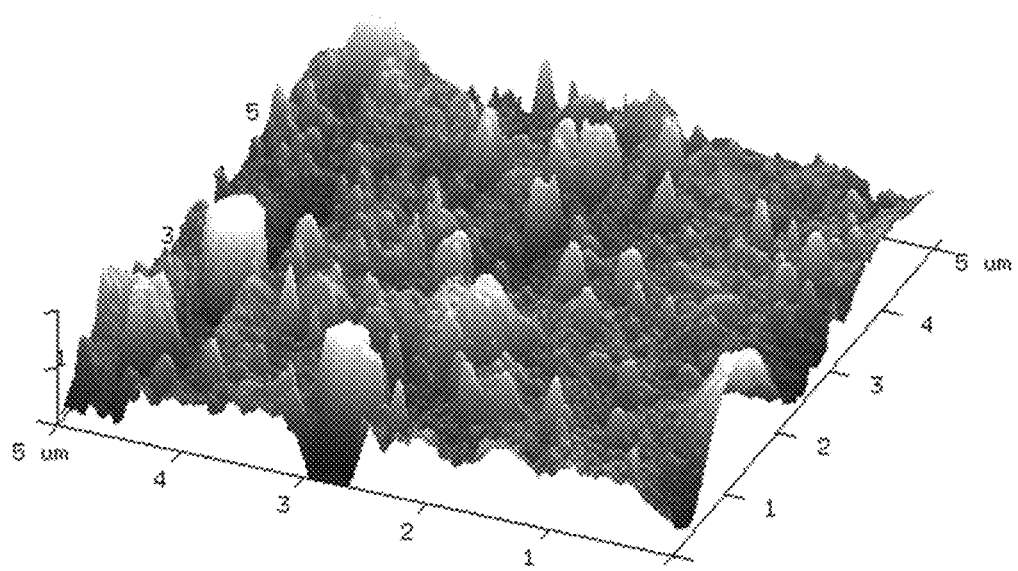
FIG. 7 shows the 3D topographical view of 5 μm×5 μm scan sizes before treatment of the skin surface sample of FIG. 1.
Figure 8:
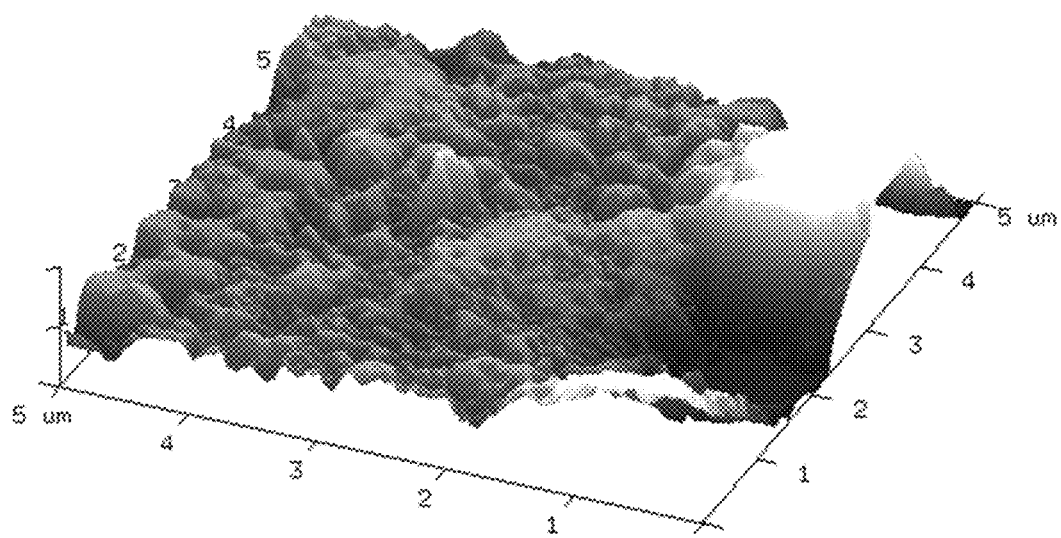
FIG. 8 shows the 3D topographical view of 5 μm×5 μm scan sizes of the skin surface sample of FIG. 2.
Figure 9:
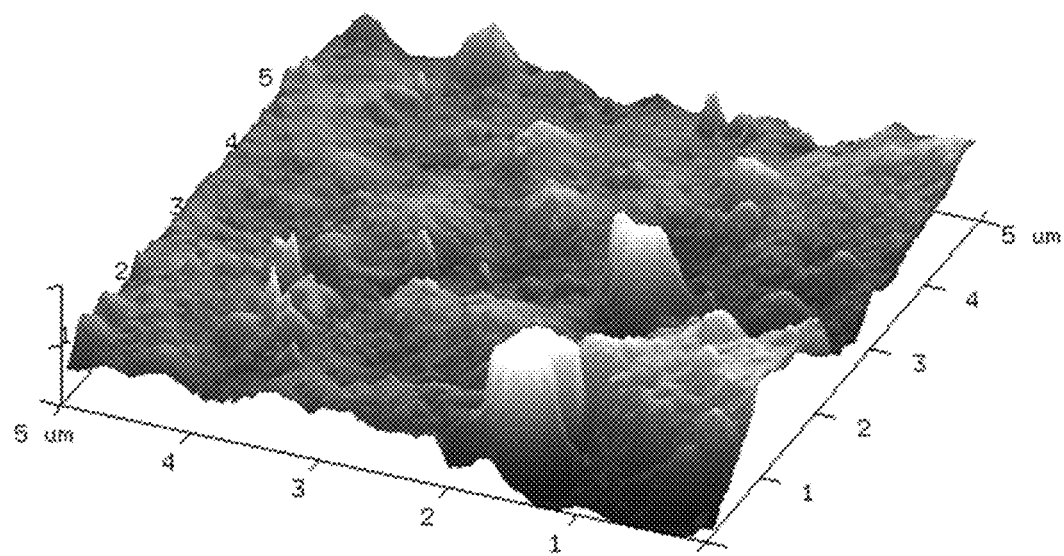
FIG. 9 shows the 3D topographical view of 5 μm×5 μm scan sizes of the skin surface sample of FIG. 3.
Figure 10:
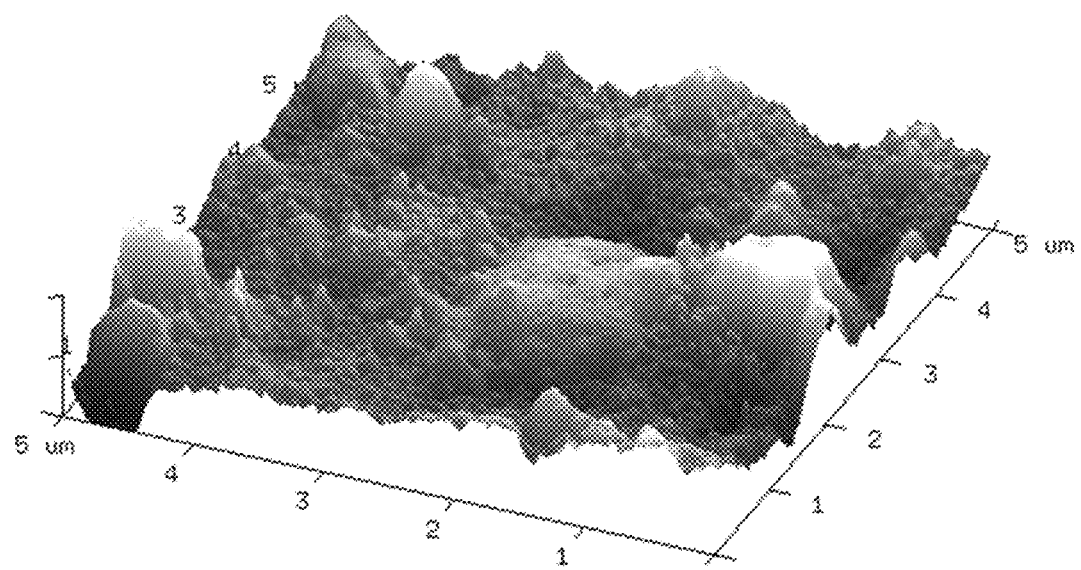
FIG. 10 shows the 3D topographical view of 5 μm×5 μm scan sizes of the skin surface sample of FIG. 4.
Figure 11:
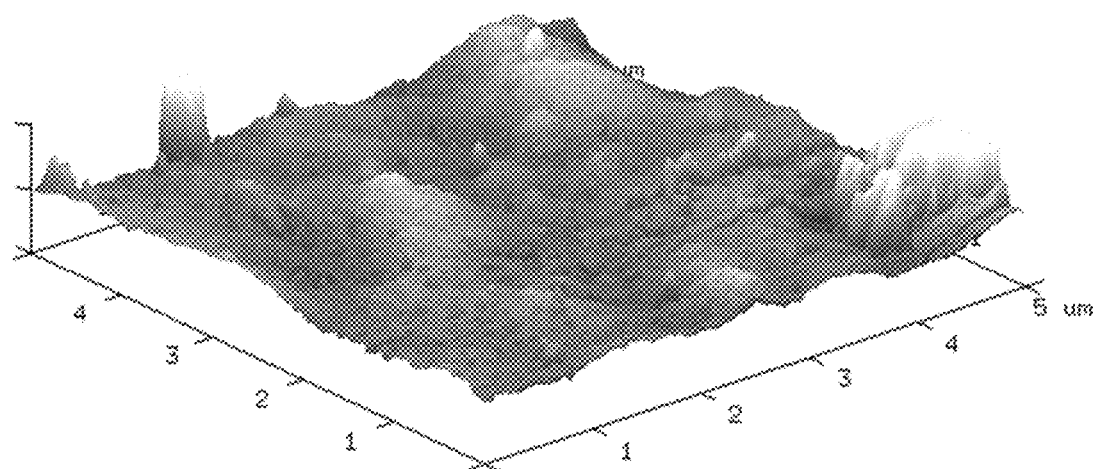
FIG. 11 shows the 3D topographical view of 5 μm×5 μm scan of the skin surface sample of FIG. 5.
Figure 12:
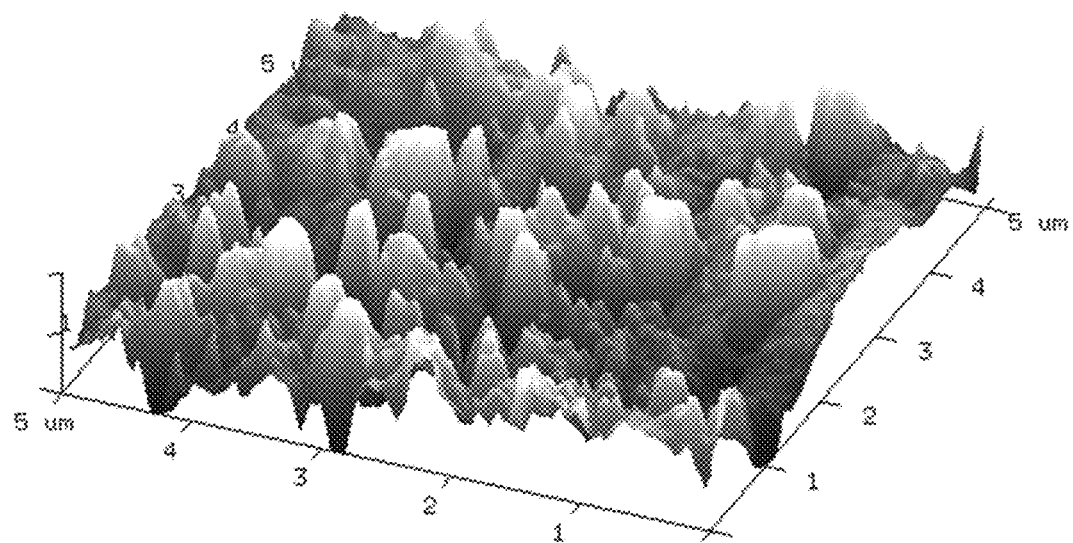
FIG. 12 shows the 3D topographical view of 5 μm×5 μm scan sizes of the skin surface sample of FIG. 6.

FIG. 7 shows the 3D topographical view of 5 μm×5 μm scan sizes of the skin sample after hydration, before any treatment. FIG. 7 was used as the baseline.

FIGS. 8, 9, 10, 11 and 12 show the profile of the surface of the skin samples after treatment with Formulation A, B, C, D or E, respectively.

Figure 13:
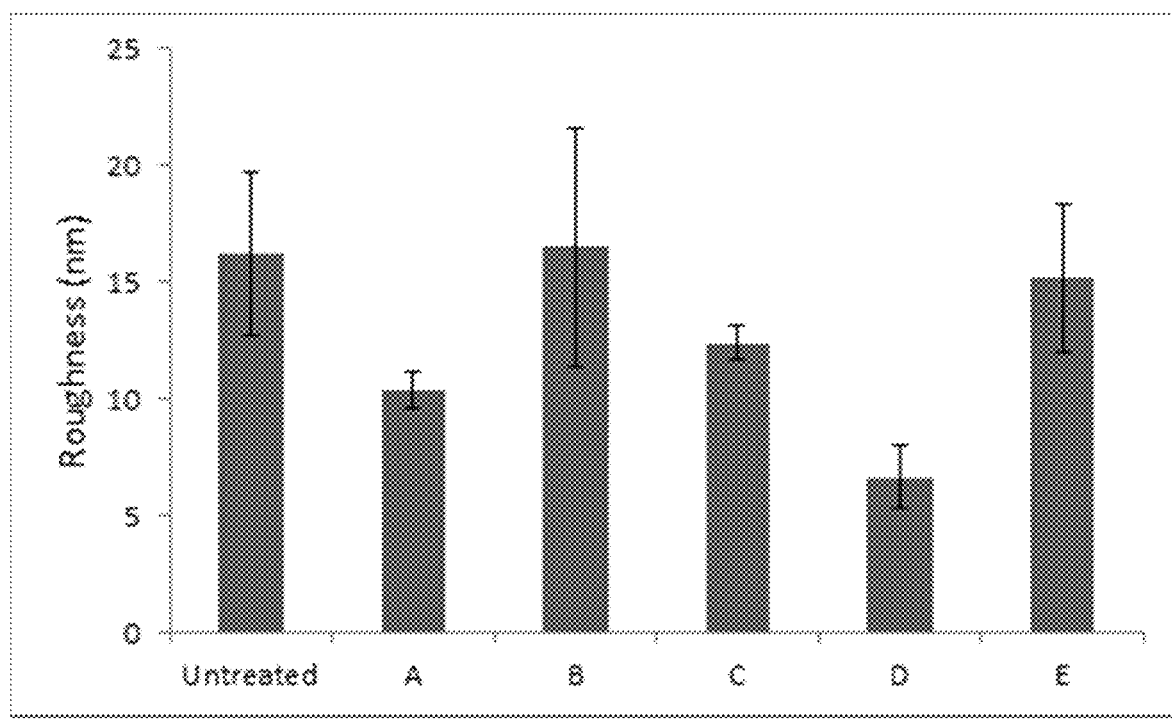
FIG. 13 shows a quantitative analysis of the smoothness determined with AFM before treatment and after treatment of the skin surface samples of FIGS. 1-6.

FIG. 13 shows the 3.5 nm×3.5 nm quantitative analysis of the roughness determined with AFM before treatment and after treatment with Formulations A, B, C, D and E.

Figure 14:
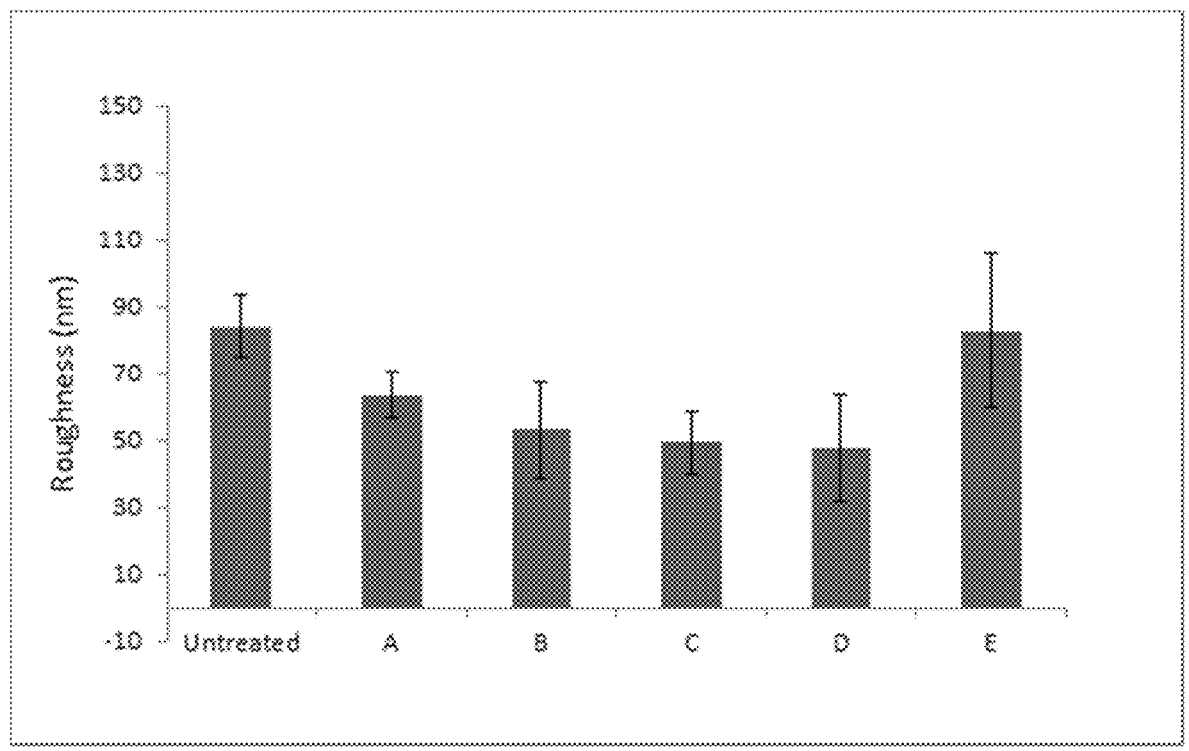
FIG. 14 shows a quantitative analysis of the smoothness determined with AFM before treatment and after treatment of the skin surface samples of FIGS. 7-12.
Figure 15:
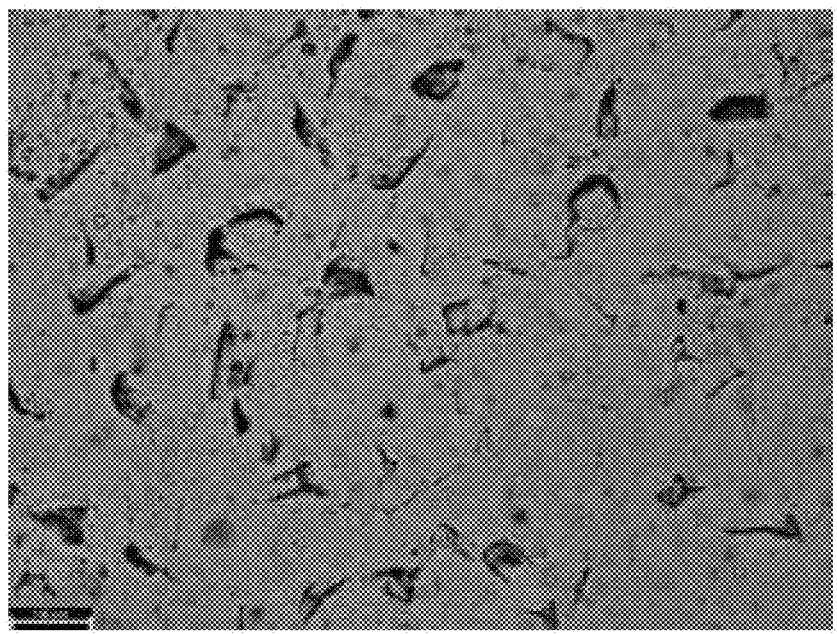
FIG. 15 shows a BrightField image of a skin sample surface before treatment with a seventh personal care formulation for use as a baseline according to aspects of the invention
Figure 16A:
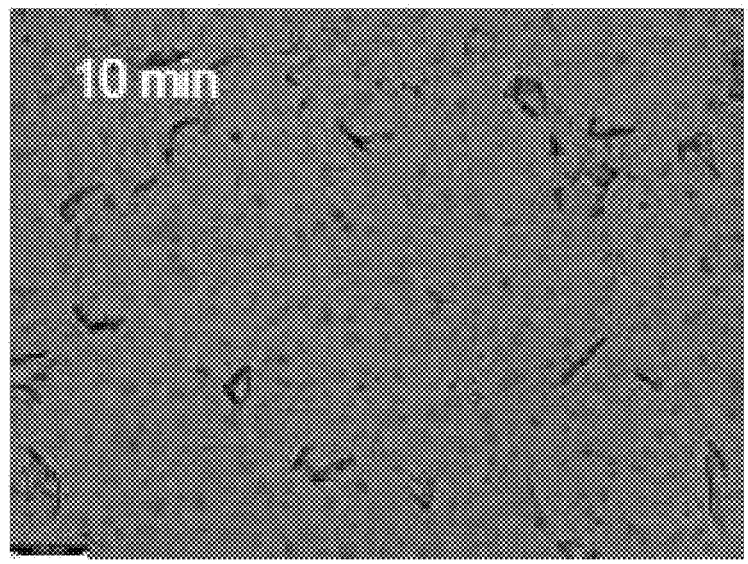
FIGS. 16A and 16B shows a BrightField image 10 minutes or 20 minutes, respectively, after treatment of the skin sample surface of FIG. 15 with the seventh personal care formulation in accordance with aspects of the invention.
Figure 16B:
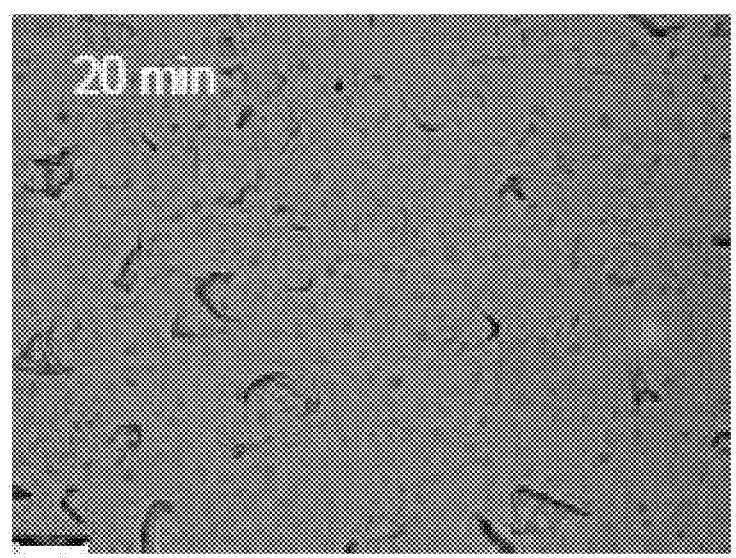
Figure 17:
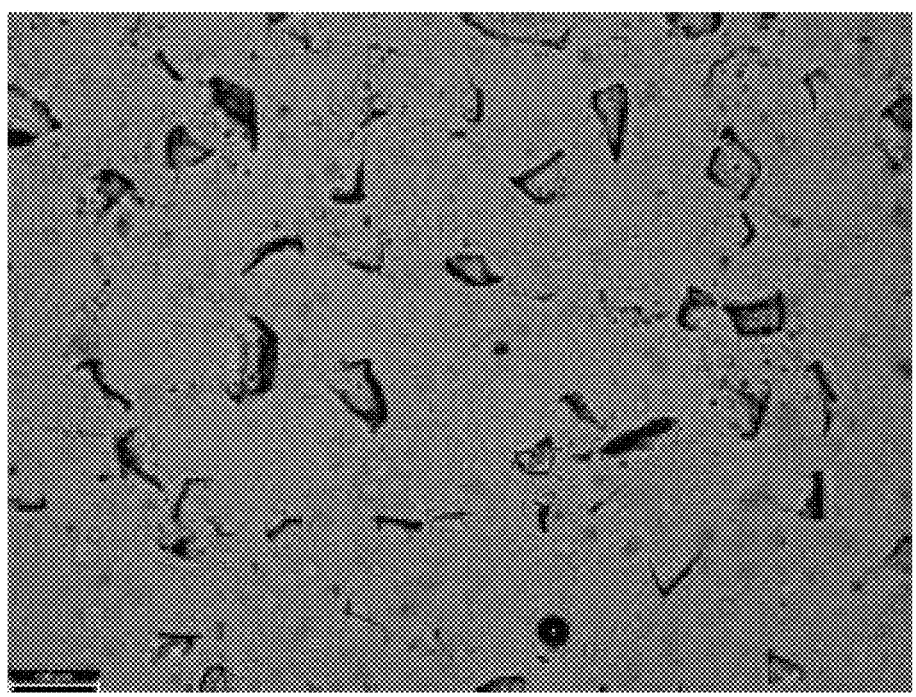
FIG. 17 shows a BrightField image of a skin sample surface before treatment with an eighth personal care formulation for use as a baseline according to aspects of the invention.
Figure 18A:
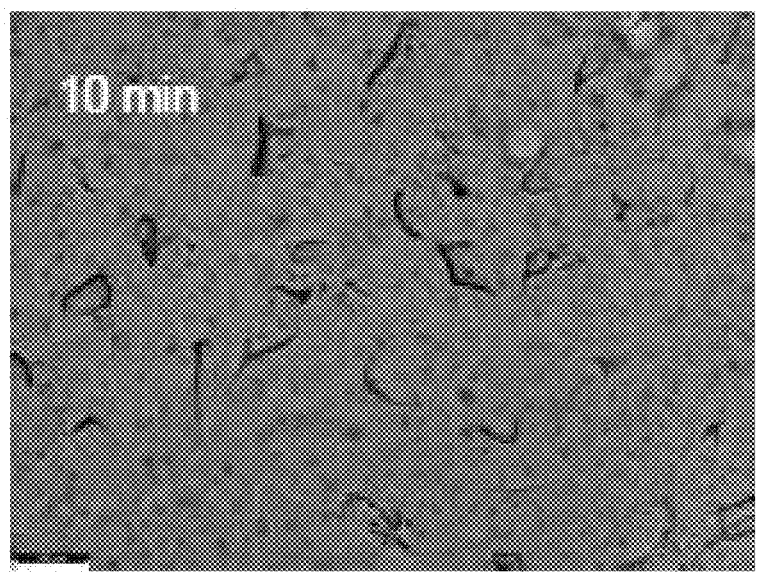
FIGS. 18A and 18B shows a BrightField image 10 minutes or 20 minutes, respectively, after treatment of the skin sample surface of FIG. 17 with the eighth personal care formulation in accordance with aspects of the invention.
Figure 18B:
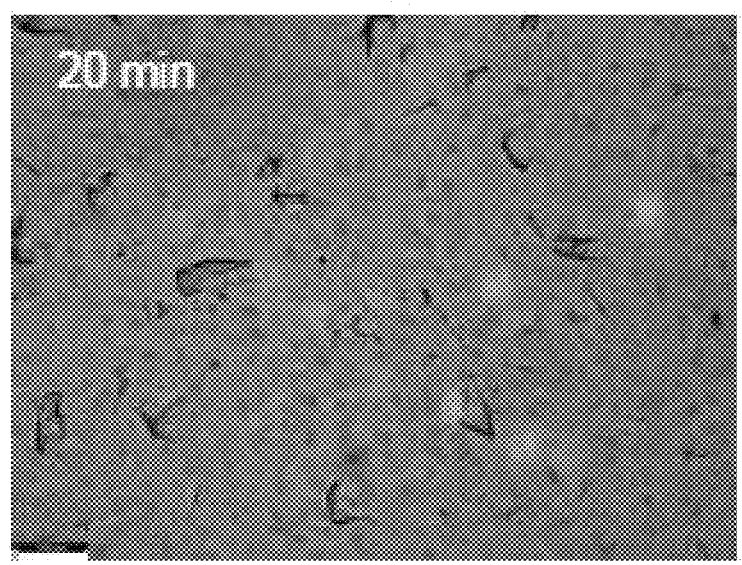

FIG. 14 shows the 30.0 nm×30.0 nm quantitative analysis of the roughness determined with AFM before treatment and after treatment with formulations A, B, C, D and E. Error bars were customized for each set of data based on 95% confidence.

For the quantitative analysis shown in graphs of FIG. 13 and FIG. 14, five to ten different areas per sample were imaged. Image processing consisted of a plane fit and 2nd order flattens. The "X" axis in 13 and FIG. 14 shows the roughness measured in [nm], where the higher the number the less smooth and the lower the number, the more smooth the skin surface.

Example 6

Additional Non-Limiting Representative Personal Care Formulations

Two non-limiting, representative personal care formulations (Examples F and G) were prepared in accordance with aspects of the invention. A summary of the formulation of Examples F and G are shown in Table 4, below.

TABLE 4

| US INCI Name | Example F (wt. %) | Example G (wt. %) |
|---|---|---|
| Witch Hazel | 18 | 18 |
| Monoalcohol | 32.41 | 32.41 |
| Lactic Acid | 15 | 15 |
| Glucanodeltalactone | 10 | |
| Salicylic Acid | 2 | 2 |
| Glycerin and Pentavitin | 3 | 3 |
| Water | 12 | 22 |
| Pentavitin and Asiaticoside | 1.2 | 1.2 |
| Phragmites Communis Extract, Centella, Tea, Chamomile, Licorice, Rosemary, Skullcap and Japanese knotweed | 1.5 | 1.5 |
| Fragrance | 0.5 | 0.5 |

Example 7

Evaluation Of Examples F And G

Samples of Examples F and G were applied to skin samples (VITRO-SKIN®) and evaluated under Light Microscopy (LM) and Atomic Force Microscopy (AFM). Specifically, 1 cm×1 cm pieces of skin samples (VITRO-SKIN®) were cleaned with hexanes to remove residual oils from the manufacturing process, and rinsed 3 times with demineralized water. The skin samples were hydrated for 30 minutes in demineralized water in an attempt to mimic physiological conditions prior to treatment. The cleaned and hydrated samples were either placed on a standard microscope slide with a coverslip for LM evaluation or mounted on a magnetic disk for AFM evaluation. The samples prepared according to the above description were utilized as the baselines.

The treatment for all the skin samples was identical. Examples F and G were tested independently on skin samples. Each skin sample was dipped into one of the personal care formulations to be tested—namely, Examples F or G—for 15 seconds and allowed to treat for 10 minutes prior to imaging. The skin samples were covered with coverslips to prevent dehydration.

Figure 19:
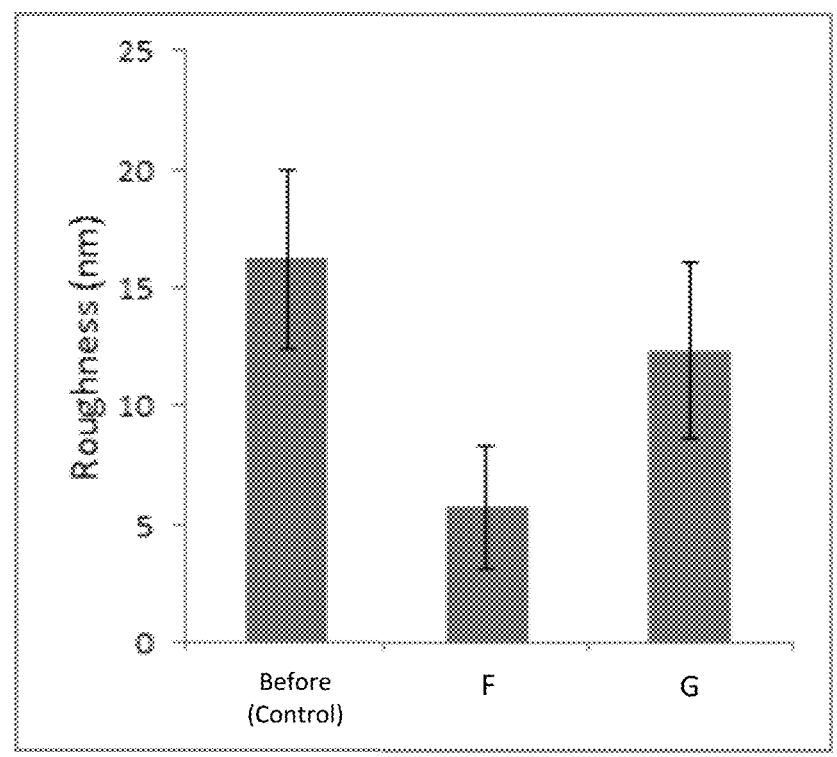
FIG. 19 shows a quantitative analysis of the smoothness determined with AFM before treatment and after treatment of the skin surface samples of FIGS. 15-18B.

The skin samples were then evaluated under procedures similar to those described in above Examples 4 and 5. Images of the skin samples are provided in FIGS. 15-18B. FIG. 19 provides a graph showing the reduction of roughness (or increase in smoothness) achieved by Examples F and G.

What is claimed is:

1. A personal care formulation comprising:
an alpha hydroxy acid;
a beta hydroxy acid;
polyhydroxy acid comprising gluconodeltalactone;
an amino acid; and
a combination of soothing antioxidants, wound healing agents, and anti-inflammatory agents;

wherein the personal care formulation has a weight ratio of alpha hydroxy acid to polyhydroxy acid of about 5:1 to about 1:4;

wherein the personal care formulation has a weight ratio of beta hydroxy acid to polyhydroxy acid of about 1:1 to about 1:11; and wherein the wound healing agent is selected from the group consisting of triterpenes, triterpenoids, oleanolic acid, maslinic acid, asiaticoside or combinations thereof.

2. The personal care formulation according to claim 1, comprising:

from about 2 to about 22 wt. % of an alpha hydroxy acid;
from about 0.5 to about 10 wt. % of a beta hydroxy acid; and
from about 2 to about 20 wt. % of polyhydroxy acid;
wherein all weight percentages are based on the total weight of the personal care formulation.

3. The personal care formulation according to claim 1, wherein the alpha hydroxy acid is selected from the group consisting of mandelic acid; glycolic acid;

citric acid; lactic acid; malic acid; tartaric acid; phytic acid; hydroxycaprylic acid; hydroxycapric acid; and a combination of two or more thereof.

4. The personal care formulation according to claim 1, wherein the beta hydroxy acid is selected from the group consisting of salicylic acid; sodium salicylate; beta hydroxybutanoic acid; tropic acid; trethocanic acid; and a combination of two or more thereof.

5. The personal care formulation according to claim 1, wherein the polyhydroxy acid further comprises galactose; lactobionic acid; or a combination thereof.

6. The personal care formulation according to claim 1, wherein the formulation is a chemical peel or an exfoliating formulation.

7. A method of improving skin appearance of a subject in need thereof, comprising applying to skin the personal care formulation according to claim 1.

8. The method according to claim 7, wherein the improvement of the skin appearance is selected from the group consisting of reducing of fine wrinkles; reducing of fine lines, reducing of pore size, exfoliating the skin; eliminating acne; toning the skin; enhancing the skin's radiance; providing smoother skin with a more uniform appearance; and a combination of two or more thereof.

9. The personal care formulation according to claim 1, wherein the amino acid is present in an amount from about 0.1 to about 7 wt. %, based on the total weight of the personal care formulation.

10. The personal care formulation according to claim 9, wherein the amino acid is selected from the group consisting of arginine; taurine; glycine; histidine; methionine; lysine; proline; leucine; and a combination of two or more thereof.

11. The personal care formulation according to claim 1, further comprising a penetration enhancing agent, optionally, in an amount from about 0.05 to about 5 wt. %, based on the total weight of the personal care formulation.

12. The personal care formulation according to claim 11, wherein the penetration enhancing agent comprises ethanol, witch hazel, or a combination thereof.

13. The personal care formulation according to claim 1, wherein the personal care formulation is free of fruit enzymes, fruit acids, metal complexes, or a combination of two or more thereof.

14. The personal care formulation according to claim 1, wherein a pH of the personal care formulation is between 2.80 and 4.10.

* * * * *